US009694062B2

(12) United States Patent
Aguiar et al.

(10) Patent No.: US 9,694,062 B2
(45) Date of Patent: Jul. 4, 2017

(54) ***PLASMODIUM FALCIPARUM* SPOROZOITE AND LIVER STAGE ANTIGENS**

(71) Applicants: Joao Aguiar, Rockville, MD (US); Keith Limbach, Gaithersburg, MD (US); Martha Sedegah, Gaithersburg, MD (US); Thomas Richie, Glenelg, MD (US)

(72) Inventors: Joao Aguiar, Rockville, MD (US); Keith Limbach, Gaithersburg, MD (US); Martha Sedegah, Gaithersburg, MD (US); Thomas Richie, Glenelg, MD (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 3 days.

(21) Appl. No.: 14/219,390

(22) Filed: Mar. 19, 2014

(65) Prior Publication Data

US 2015/0265690 A1 Sep. 24, 2015

(51) Int. Cl.

| | |
|---|---|
| ***A61K 38/00*** | (2006.01) |
| ***A61K 39/00*** | (2006.01) |
| ***A61K 39/002*** | (2006.01) |
| ***C12N 15/86*** | (2006.01) |
| ***A61K 39/015*** | (2006.01) |
| ***C07K 14/445*** | (2006.01) |

(52) U.S. Cl.

CPC .......... *A61K 39/015* (2013.01); *C07K 14/445* (2013.01); *A61K 2039/53* (2013.01); *A61K 2039/545* (2013.01); *C12N 2799/023* (2013.01); *C12N 2799/04* (2013.01)

(58) Field of Classification Search

CPC ...... A61K 38/00; A61K 39/00; A61K 39/002; A61K 2039/5156; A61K 2039/523; A61K 2300/00; C07K 14/44; C07K 14/445; C12N 15/86; C12N 2760/16134

See application file for complete search history.

(56) References Cited

U.S. PATENT DOCUMENTS

2008/0260762 A1* 10/2008 Grey ...................... A61K 39/02 424/185.1
2008/0260763 A1* 10/2008 Felgner ................ A61K 39/015 424/186.1

FOREIGN PATENT DOCUMENTS

WO WO 2006/088492 * 8/2006 ............... C12Q 1/68

* cited by examiner

*Primary Examiner* — Ja'na Hines

(74) *Attorney, Agent, or Firm* — Albert M. Churilla; Ning Yang

(57) ABSTRACT

The invention provides novel malaria polypeptides expressed at the pre-erythrocytic stage of the malaria life-cycle. The antigens can be utilized to induce an immune response against malaria in a mammal by administering the antigens in vaccine formulations or expressing the antigens in DNA or other nucleic acid expression systems delivered as a vaccine formulation.

12 Claims, 8 Drawing Sheets

Panel A

Panel B

PF 61

PF 56

PF 121

PF 144

*PLASMODIUM FALCIPARUM* SPOROZOITE AND LIVER STAGE ANTIGENS

CROSS-REFERENCES TO RELATED APPLICATIONS

This application is a Divisional Application of U.S. application Ser. No. 12/938,448 filed Nov. 3, 2010, which claims the benefit of U.S. Provisional Application No. 61/272,809, filed 5 Nov. 2009, which are incorporated herein by reference.

BACKGROUND OF INVENTION

1. Field of Invention

The inventive subject matter relates to DNA sequences and polypeptides from *Plasmodium falciparum* for use as an anti-malaria vaccine component and methods of inducing an immune response to these antigens.

2. Background Art

Malaria is caused by the vector borne organism *Plasmodium* spp. The parasite has a complex lifecycle requiring stage specific expression of proteins. These proteins can be expressed at different stages or be specific to stages. Malaria is an extremely important disease, with over 3 billion people living in malaria endemic areas. Over 1 million deaths are attributable to malaria per year. The emergence of drug resistant strains has compounded the problem of treating the disease. Unfortunately, no FDA-approved vaccine exists.

The entire genomic sequence of *P. falciparum* has been sequenced (Bowman et al., Nature, 400: 532-538 (1999), Gardner, et al., Nature, 419: 498-511 (2002)). The rodent malaria parasite, *P. yoelii* has also been sequenced (Carlton et al., Nature, 419: 512-519 (2002)). Despite this, however, the development of efficacious anti-malaria vaccines has been severely hampered by the paucity of promising antigens. Sequencing of the *Plasmodium falciparum* and *Plasmodium yoelii* genomes yielding identification over 5,200 genes in the genome. However, despite the large number of potential gene targets, use of the data set alone will not likely result in new vaccine constructs. Consequently, only 0.2% of the *P. falciparum* proteome is undergoing clinical testing. Moreover, these vaccine candidate antigens have failed to induce high grade protection in volunteers. Nevertheless, immunization of mice and humans with radiation-attenuated sporozoites results in a high-grade immunity (>90%), suggesting that development of effective anti-malaria vaccines is possible. This protective immunity appears to target multiple sporozoite and liver stage antigens.

SUMMARY OF THE INVENTION

The invention relates DNA sequences encoding recombinant *Plasmodium falciparum* proteins. The proteins were identified from a large panel of *P. falciparum* proteins. These were evaluated based on a number of criteria, judged to be relevant to protection against malaria. The sequences can be utilized to express the encoded proteins for use as subunit immunogenic antigens or can be incorporated into vectors suitable for in vivo expression in a host in order to induce an immunogenic response. The proteins can be utilized in combination or singly in immunogenic formulations.

In one embodiment, the compounds can be used as immunogenic proteins. In this embodiment, the proteins can be produced by first inserting the DNA encoding the proteins in suitable expression systems. The expressed and purified proteins can then be administered in one or multiple doses to a mammal, such as humans. In this embodiment, the purified proteins can be expressed individually or DNA encoding specific proteins can be recombinantly associated to form a single immunogenic composition. These immunogenic compositions can then be administered in one or multiple doses to induce an immunogenic response.

In an alternative embodiment, DNA encoding the proteins can be inserted into suitable vector expression systems. These include, for example, adenoviral based systems, such as in Bruder, et al (patent application publication number US 20080248060, published Oct. 9, 2008) or a DNA plasmid system.

DETAILED DESCRIPTION OF PREFERRED EMBODIMENTS

Figure 1:
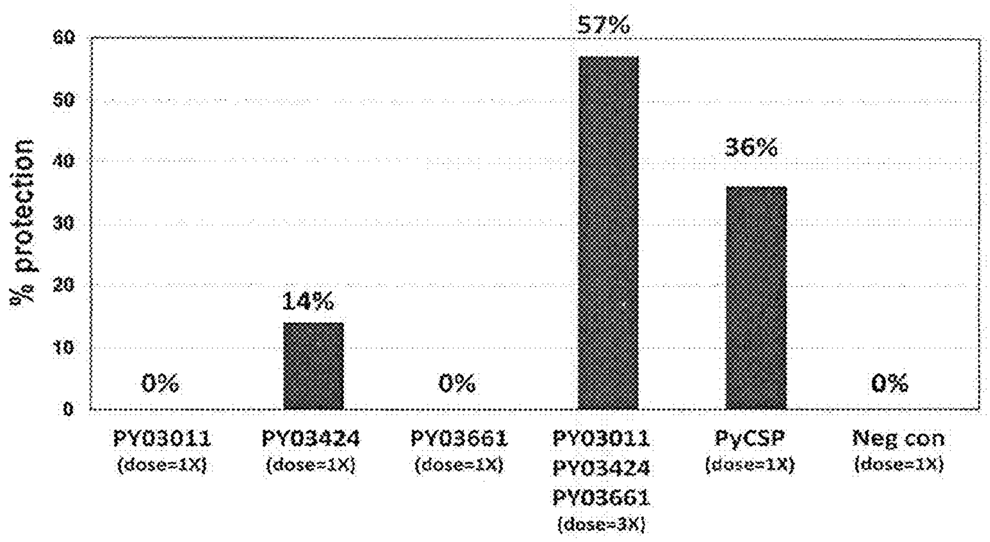
FIG. 1. Protection of mice immunized (primed) with a with 100 μg of DNA *P. yoelii* vector containing the indicated insert. Mice receiving more than one insert are indicated as receiving multiple doses (i.e., dose=1× to 3×). The mice were boosted, on day 40, with vaccinia-*P. yoelii* vector containing the same insert as priming dosage. On day 50, the mice were challenged with *P. yoelii* sporozoites and at day 61-68, parasitemia was evaluated. In these experiments, N=14.
Figure 1:
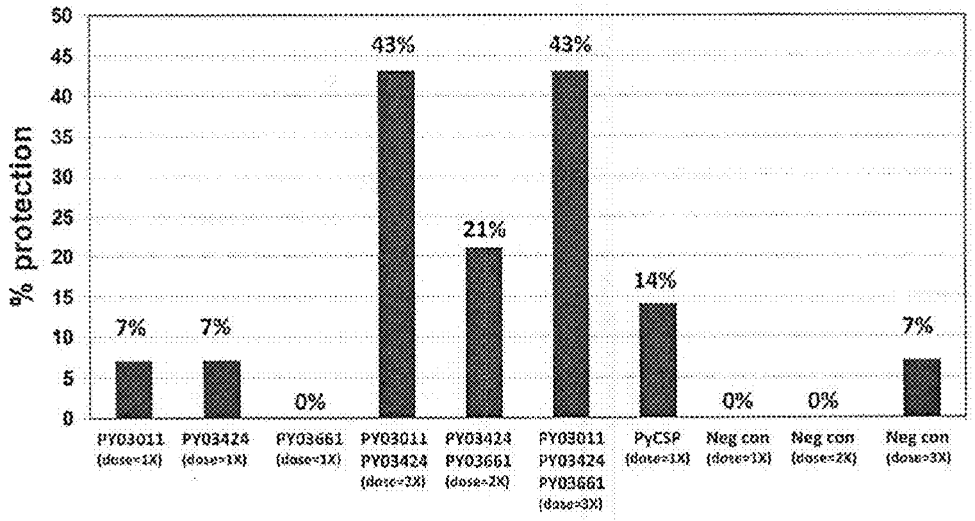

One embodiment of the invention relates to isolated proteins expressed at the pre-erythrocytic stage of the malaria (i.e., *Plasmodium falciparum*) life-cycle. The isolated proteins can be incorporated in immunogenic formulations in order to induce an immune response. In this embodiment, the proteins can be incorporated singly or in combination. The immunogenic compositions of the invention also include adjuvants to improve or enhance the immune response elicited by the polypeptides. A further aspect of the invention is the ability of the proteins to induce an humoral and/or T-cell immune response.

As used herein, the term "polypeptide" refers to a polymer of amino acids and does not refer to a specific length of the product. Proteins are included within the definition of polypeptides. The term "mer", in conjunction with a number, such as 15-mer, refers to the length of a polypeptide in numbers of amino acids.

Methods of predicting immunogenic regions, including predicting T-cell epitopes or HLA binding regions in a polypeptide are well-known in the art. The term "motif" refers to a polypeptide with a specific amino acid sequence that has been predicted to associate or bind to an HLA molecule.

As used herein, the proteins may be prepared for inclusion of an effective amount of one or more polypeptides described herein into an immunogenic composition by first expressing the appropriate gene fragments by molecular methods, expression from plasmids or other expression systems such as viral systems and then isolated.

An embodiment of the invention is the incorporation of DNA encoding the polypeptides in vector expression systems, wherein the system permits expression of one or more polypeptides in mammalian host cells, such as in humans to induce an immune response. The expression systems can be DNA plasmids or viral systems. Methods for preparing and administering a DNA vaccine expressing *Plasmodium* proteins are well known in the art and have been previously described (e.g., Doolan and Hoffman (2001), Int J. Parasitol. 31: 753-62; U.S. Patent Publication 2008/0248060 (Oct. 9, 2008)), herein incorporated by reference.

In another embodiment, derivatives of the proteins can be used in immunogenic compositions. In a variant of this embodiment, the immunogenic derivatives of the *P. falciparum* proteins include at least 10 contiguous amino acids of an amino acid sequence of a full length polypeptide comprising an amino acid sequence selected from the group consisting of SEQ ID NOs: 2, 4, 6, 8, 10, 12 and 14. Immunogenic derivatives of the polypeptides may be prepared by expresson of the appropriate gene fragments or by other methods such as by peptide synthesis. Additionally, derivatives may be a fusion polypeptide containing additional sequence encoding one or more epitopes of the *P. falciparum* polypeptides of selected from the group consisting of SEQ ID NOs: 2, 4, 6, 8, 10, 12 and 14. In these embodiments, the proteins can be directly incorporated in immunogenic formulations or expressed from DNA plasmids or viral expression systems.

In some embodiments, the *P. falciparum* polypeptides include immunogenic derivatives with more than 80% amino acid sequence identity to the sequences of selected from the group consisting of SEQ ID NOs: 2, 4, 6, 8, 10, 12 and 14. In this context, the term "identity" refers to two or more sequences or subsequences that are the same or have a specified percentage of amino acid residues that are the same, when aligned for maximum correspondence. Where sequences differ in conservative substitutions, i.e., substitution of residues with identical properties, the percent sequence identity may be adjusted upwards to correct for the conservative nature of the substitution.

Immunization of mice with irradiation-attenuated sporozoites elicits a strong protective immunity (Clyde et al., Am. J. Med. Sci, 266: 398-401 (1973a); Clyde et al., AM. J. Med. Sci, 266: 169-177 (1973b); Nussenzweig et al., Nature, 216: 160-162 (1967)). Use of irradiation-attenuated sporozoites, as a vaccine approach, appears to target multiple antigens, many of which are pre-erythrocytic, as evidenced by the identification of genetically restricted responses to pre-erythrocytic stage antigens other than CSP in volunteers immunized with the irradiated sporozoite vaccine (ISV). (Kryzch et al., J. Immunol, 155: 4072-4077 (1995); Wizel et al., J. Immunol., 155: 766-775 (1995a); Wizel et al., J. Exp. Med., 182: 1435-1445 (1995b)). Targeting of pre-erythrocytic stage antigens with the irradiation-attenuated vaccine leads to immunity against sporozoites or infected hepatocytes and, therefore, prevents the onset of blood infection by blocking the release of primary merozoites into the blood stream.

Pre-erythrocytic proteins are likely critical in conferring protective immunity against malaria. Despite the relatively large number of malaria genes that have been identified, following sequencing of the malaria parasite genome, identification of anti-malaria drug vaccine candidates has been hampered, to a great extent, by the relatively complex life-cycle of malaria parasite. Furthermore, many genes of the malaria parasite are poorly defined, antigenically, as well as functionally. Therefore, high-throughput characterization of antigens encoded by numerous genes was undertaken in order to ascertain potential protective responses. Based on these responses specific genes were selected as potential vaccine formulations.

Example 1: Identification and Expression of *P. falciparum* Proteins

Characterization of identified sequences requires the availability of effective protein expression platforms. This limitation has been problematic in the development of anti-malaria vaccines. In order to circumvent this restriction, a modified wheat germ cell-free system was employed for parallel expression and screening of recombinant proteins. A panel of 150 putative *P. falciparum* pre-erythrocytic stage genes was established, based on bioinformatic analysis and transciptome and proteome expression databases for sporozoite and liver stage parasites. Most of the genes in this list encode hypothetical proteins with unknown function. It was hypothesized that some of the genes in this panel could serve as vaccine antigens, as evidenced by immune reactivity to sera from irradiated sporozoite vaccine (ISV)—immunized volunteers.

Use of other expression systems proved difficult for further, necessary down-stream analysis and characterization. In order to improve expression, a modified wheat germ cell-free expression system was utilized. This system permitted expression of approximately 90% of clones evaluated. Genes selected, for further expression and characterization, were identified, based on proteome and/or transcriptome datasets, by their expression at the pre-erythrocytic stage. A total of 155 genes of *P. falciparum* were used to generate protein expression DNA constructs as GST- and 6× His-fusions using the pE-E01-GST-TEV-GW and pEU-E01-His-TEV-GW plasmids, respectively (Tsuboi, et al., 2008).

Expression of Recombinant Proteins.

The expression of recombinant proteins was conducted utilizing a wheat germ cell-free system. Gene-specific RNAs to be used as template in the in vitro translation reactions were synthesized in two scales:

a. Small-scale. The small-scale batch-reaction was performed with all clones by first generating RNAse-free PCR DNAs and using them as templates in transcription reactions. Individual genes were PCR-amplified from plasmid mini-prep DNA using pEU-E01-specific primers and adapters. Primers used were SP6: 5' AGAGCGCGCAAGACGCGCAGGACCG 3'; E01: 5' AGAGAGAGAGAGA ACAACAACACAAACA 3'.

All PCR-amplified gene sizes were confirmed in an agarose gel. Transcription reactions were set up with 2 µl of PCR DNA template, 25 mM dNTPs, 1 U/µl RNAse inhibitor, 1.2 U/µl SP6 Polymerase and transcription buffer for 6 hours at 37° C. The sizes of the gene-specific transcripts were verified by agarose gel electrophoresis. The RNAs were ethanol-precipitated to remove unwanted transcription reagents, dissolved in RNAase-free water and used for protein expression reactions.

b. Large-scale. The synthesis of RNAs for large-scale protein expression was performed using RNAse-free plasmid DNA as template, purified by a standard DNA isolation kit, and added directly into the transcription reactions as follows: 25 µg of plasmid DNA were mixed with 2.5 mM of NTPs, 1 U/µl of RNAsin, 1 U/µl of SP6 polymerase in transcription buffer described above. The total reaction volume was 250 µl and incubated at 37° C. for 6 hours. The qualities of all expressed RNAs were analyzed by agarose gel electrophoresis prior to setting up the translation reactions.

As with RNA synthesis, recombinant proteins were expressed in two scales throughout this study, as follows:

a. Small Scale. Batch reactions were set up in 96-well U-bottom plates using a protocol described earlier (Sawasaki et al., FEBS Lett, 514: 102-105 (2002b). Briefly, the reaction was assembled by overlaying 40 µl of substrate mix (0.45 mg/ml Creatine kinase, 20 U of RNasin, 24 mM Hepes/KOH pH 7.8, 100 mM KOAc, 2.7 mM Mg(OAc), 0.4 mM Spermedine, 2.5 mM DTT, 1.2 mM ATP, 0.25 mM GTP, 16 mM Creatine-Phosphate, 0.005% NaN3 and 0.3 mM of each of the amino acids including [14C]leucine (2 µCi/ml)) over 10 µl of translation mix containing 2 µl of each RNA and 8 µl of wheat germ extract OD240 (OD60 final concentration). The extract was purchased from CFSciences, Yokohama, Japan. However, other comparable sources can be used. The plate was covered with parafilm and incubated at 26° C. for 16 hours.

b. Large-Scale. Large amounts of recombinant proteins were synthesized following general guidelines recommended by the manufacturer of the wheat germ extract (i.e., CFSciences, Yokohama, Japan). Depending on the specific quantity needs for each protein, variable numbers of reactions were set up using flat bottom 6-well plates. Each translation reaction contains a bilayer of 2 mixtures; the lower portion includes a total of 500 µl of the transcribed RNA and the wheat germ extract and the upper mixture consists of 5.5 ml of dialysis buffer. In brief, the lower reaction mixture was prepared by mixing 250 µl of the RNA reaction, 40 mg/ml creatine kinase and 120 OD/ml of wheat germ extract (WGE OD240, CFSciences, Yokohama, Japan). This lower mixture was transferred to a 6-well and carefully overlaid with 5.5 ml of sub-admix buffer supplied by the manufacturer (CFSciences, Yokohama, Japan) in order to form a bilayer reaction. Plates were sealed with parafilm and translation occurred at room temperature overnight.

Purification of Proteins.

Recombinant proteins tagged with GST were affinity-purified using a procedure that has been previously described (Tsuboi et al., Infect. Immun., 76: 1702-1708 (2008)). After translation reaction was complete, the protein-containing mix was absorbed into Glutathione Sepharose 4B resin (GE healthcare, Piscataway, N.J.) followed by protein elution with 20 U of tobacco etch virus protease (AcTEV™, Invitrogen, Carlsbad, Calif.) and 1 mM of DTT. Eluted proteins were confirmed by SDS-PAGE stained by Coomassie blue or silver stains. Purified protein concentrations were determined by both Bradford protein assay kit and spectrophotometer and reported as µg/ml.

Expressed proteins were further characterized by in vitro and in vivo analysis. In vitro analysis included antibody based and T-cell mediated assays. Analysis of the selected genes were analyzed using the following methodologies:

Example 2: Assay Methods in Analysis of Pre-Erythrocytic Gene Products

Indirect Fluorescence Antibody Assay (IFA).

Sera from both mice and rabbits immunized with all proteins were tested for immune-reactivity to sporozoite, 4- and 6-day old exo-erythrocytic, asexual and sexual erytrocytic stages of *P. falciparum*. IFA protocols for testing sera against sporozoite and erythrocytic stages were as described in Aguiar et al., Vaccine, 20: 275-280 (2001).

Liver stage parasites were generated and tested by two different methods. The first used in vitro generated liver stages by infecting $5\times10^4$ HC04 hepatocytes (Sattabongkot et al., Am J Trop Med Hyg., 74: 708-715 (2006)) with $5\times10^5$ *P. falciparum* sporozoites. After a brief incubation period of 4-6 hours, cells were washed and parasites were left to develop for a period of 2-, 4- and 6-days. Before infected hepatocytes were tested in IFA, cells were stained with Lysotracker™ (Invitrogen, Carlsbad, Calif.) following manufacturer's protocol and fixed with acetone. The second method used *P. falciparum*-infected liver stages parasite generated in chimeric mice as reported in a study describing this novel method (Sacci et al., Int J Parasitol., 36: 353-360 (2006)).

In summary, mice were infected with $1.5\times10^6$ *P. falciparum* sporozoites and their livers harvested between 3 and 8 days post-infection for cryosectioning. Selected lobes were embedded in tissue-Tek O.C.T.™ compound (Miles Scientific, Naperville, Ill.) and frozen in an isopentane/liquid nitrogen bath. Tissue sections (7 µm) were cut on a Leica CM1900™ (Leica Microsystems, Deerfield, Ill.), fixed in absolute methanol and stored at −80° C. until used. IFA on both types of infected hepatocytes were done with mouse and rabbit polyclonal sera at single 1:100 dilution. As a positive control, anti-heat shock protein-70 antibody was utilized. The IFA was developed by incubating cells with FITC-conjugated anti-mouse or anti-rabbit IgG and staining the nuclei with Hoechst 33258 pentahydrate. Slides were mounted in anti-fading Vectashield™ (Vector Laboratories, Burlingame, Calif.) and visualized by confocal microscopy.

Immuno Electron Microscopy.

The ultrastructural localization of *Plasmodium* antigen expression was examined by immunoelectron microscopy. Briefly, *P. falciparum* infected red blood cells and salivary glands *P. falciparum* infected *Anopheles stephensi* were fixed in PBS containing 1% paraformaldehyde, and 0.1% glutaraldehyde, for 24 h at room temperature. Ultra thin sections, embedded in LR-White™ resin (Polyscience, Inc., Warrington, Pa.) were cut and placed on nickel grids. The sections on the grids were etched by incubation with freshly prepared, saturated sodium-m-periodate for 5 minutes, followed by rinsing 3 times in deionized water. The grids were quenched with 0.1 M glycine in phosphate buffer for 20 minutes to prevent any free aldehyde groups from binding to the primary antibody. The grids were blocked by incubation in PBS, 1% BSA, 5% Fish gelatin for 30 minutes.

Grids were incubated with the primary antibody (diluted 1:50) in a humidified environment for 2 hours, followed by washing 5 times in PBS-0.1% Tween-20 (polyoxyethylene (20) sorbitan monolaurate). The grids were then incubated for 30 minutes with a goat anti-mouse or rabbit antibody conjugated to 10 nm gold particles. The grids were washed as described above, then post-stained with 2% Uranyl acetate and rinsed with water.

The sections were examined with a transmission electron microscope. Negative controls included uninfected cells and the use of nonspecific, irrelevant antibodies as the primary antibody.

Western Blotting.

Recombinant proteins were analyzed by Western blot using two protocol, summarized as follows:

a. For the high throughput expression, [$^{14}$C]Leucine-labeled proteins were separated by SDS-PAGE as three fractions; 2 μl of the total translation reaction (T), after the 96-well plate was spun 2 μl of supernatant (S) fraction and lastly the pellet (P) was re-suspended in sample buffer and separated as pellet fraction. Recombinant proteins were identified by autoradiography using an imaging analyzer.

b. Purified recombinant proteins were screened using the regular Western blot protocol. Ten micrograms of each protein were separated on a pre-cast 4-20% gradient SDS polyacrylamide gel, and subsequently electrotransferred onto a PVDF membrane. Western blot with a 1:500 dilution of rabbit antisera immunized with the proteins or human immune sera. Peroxidase-conjugated goat anti-rabbit or human IgG antibody was used as the secondary antibody at a dilution of 1:10,000. The reaction was developed using ECL-Plus™ (General Electric Healthcare, Piscataway, N.J.) western blotting detection system according to the manufacturer's instructions.

Enzyme-Linked ImmunoSorbent Assay (ELISA).

Human sera, from volunteers immunized with ISV, were tested at 1:100 dilutions for antigen-specific reactivity measured by ELISA using recombinant proteins expressed by both small and large scale methodologies, as described in Example 1. Negative (GST and wheat germ extract) and positive (CSP and SSP2/Trap) control proteins were also expressed in the same scale. Immunolon II™ ELISA plates (Dynatech Laboratory Inc., Chantilly, Va.) were coated with 2-5 μl of recombinant protein and wheat germ extract in PBS overnight at room temperature. Wells were washed three times with PBS containing 0.05% Tween 20 (polyoxethylene (20) sorbitan monolaurate) (washing buffer) and blocked with 100 μl of 5% non-fat dry milk in PBS (blocking buffer) for 2 hours at 4° C. After washing three times, wells were incubated for 2 hours with 50 μl of 1:100 dilution of test human sera. The wells were again washed three times and incubated for 1 hour with peroxidase-labeled goat anti-human IgG (KPL). After a three washes the wells were incubated for 20 minutes with 100 μl of a solution containing ABTS substrate [2,2'-azino-di-(3 ethylbenzthiazoline sulfonate] and $H_2O_2$. Color reaction was measured in a micro-ELISA automated reader at OD 410 nm. ELISA data were presented as the average of OD readings for tested sera dilutions. The sporozoite-specific antibodies in these human sera were assessed by the indirect fluorescent antibody test (IFAT) as previously described. Results were reported as the endpoint dilution, representing the last serum dilution at which fluorescence was scored as positive.

Interferon γ ELIspot Assay.

Multiscreen MAIPS4510™ plates (Millipore, Billerica, Mass.) were coated with 100 μl well of sterile carbonate/bicarbonate buffer containing 15 μg/ml of anti-human IFN-γ mAb 1-D1K (purchased from Mabtech, Cincinnati, Ohio) overnight at 4° C. Plates were washed five times with 100 μl/well RPMI medium containing 25 mM HEPES buffer and L-glutamine.

The plates were blocked with 200 μl/well HR-10 media containing 1% of the following: 200 mM L-glutamine, Pen/Strep, 10 mM MEM, 10% Human AB Serum and 87% RPMI medium. The plates were incubated with blocking solution at 4° C. for at least 24 hours. PBMCs (20×$10^6$) were thawed at 37° C. and resuspended in 10 mls R-10 media containing 10% FBS, 1% 200 mM L-glutamine, 1% Pen/Strep and 88% RPMI. The cells were washed twice at 1200 rpm, 25° C., 10 minutes and again with 10 mls R-10 and pelleted at 1000 rpm, 25° C., 10 minutes. The cells were re-suspended in an appropriate volume of HR-10 for counting. The volume of the cell suspension was increased with HR-10 and rested overnight at 37° C./5% CO2 incubator. Cells were counted again to calculate recovery and viability. The plates were washed from their block solution six times with RPMI medium and left at room temperature until the stimulants and cell suspension were prepared. The stimulants were diluted with HR-10 media to its optimal concentration. The cell suspension was diluted with HR-10 to its optimal concentration. The stimulants were added first to the α-IFN-γ coated wells in quadruplicate at 100 μl/well followed by the addition of 100 μl/well cell suspension at a final concentrations of 100,000, 200,000 and 400,000 cells/well. Non-stimulant containing wells contained HR-10 media and the cell suspension were used as background controls. Plates were incubated for 36 hours at 37° C./5% CO2 then washed six times with 1×PBS+0.05% Tween-20 (polyoxethylene (20) sorbitan monolaurate) solution. ELIspot was developed by adding 100 μl of 1 μg/ml biotinylated α-IFN-γ mAb 7-B6-1 (purchased from Mabtech, Cincinnati, Ohio) and incubated at room temperature for three hours. Plates were washed six times with 1×PBS+0.05% Tween-20 (polyoxethylene (20) sorbitan monolaurate) solution. Development was performed by adding 100 μl of a 1:1000 streptavidin-alkaline phosphatase solution and incubated at room temperature for one hour. Plates were washed six times with 1×PBS+0.05% Tween-20 (polyoxethylene (20) sorbitan monolaurate) followed by three washes with 1×PBS solution. Alkaline Phosphatase Conjugate at 1:25 dilution was added and incubated at room temperature for 15 minutes. The chromogenic reaction was stopped by extensively washing the plates with water. Once dry, the spots were counted using the AID™ ELIspot plate reader (Strassberg, Germany).

Example 3: Immunogenicity and Life Cycle Expression of Pre-Erythrocytic *P. falciparum* Genes A summary of the expression and reactivity of 22 genes is shown in Table 1. An important aspect of the proteins in Table 1 is that they were recognized by human antibody and/or T-cells from volunteers immunized with IVS. Therefore, since they are recognized within the natural immune response against malaria sporozoites these proteins may be valuable in conferring immunity against malaria.

Expressed proteins from all genes in Table 1 were recognized by ELISA and/or by Western blot analysis using ISV-immunized human sera. Additionally, some antigens were also recognized by immune T cells. This illustrates that the novel antigens exist within the natural structure of malaria sporozoites used for ISV immunization. Furthermore, the antigens are recognized as foreign to the human body and are therefore capable of eliciting a protective immune response. Additionally, reactivity of the sera also indicates that these antigens are associated with complete protection against malaria infection in these volunteers, which further indicates that these antigens are potential vaccine candidate antigens. The genes shown in Table 1 have been verified as being expressed at the pre-erythrocytic (sporozoite and liver) parasite stages by IFA. The antigen's subcellular localization was also determined by electron microscopy (EM).

*P. falciparum* proteins in Table 1 expressed from the cloned sequences were recognized by human antibodies and/or T cells from volunteers immunized with ISV. As such, the novel proteins are recognized within the natural immune response against malaria sporozoites. Therefore, these proteins may be important in immunity against malaria.

*P. yoelii* vaccine vector containing the same *P. yoelii* insert. Mice immunized with a combination of vectors expressing PY03011, PY03424 and PY03661 were primed with a total of 300 μg of DNA-*P. yoelii* vectors and boosted with a total of $1.5\times10^8$ pfu of the vaccinia-*P. yoelii* vectors. On day 50, the mice were bled and sera prepared. On day 54, the mice were challenged with 300 *P. yoelii* sporozoitses. On days 61-68, parasitemia was evaluated by visualization of Giemsa-stained blood smears. Mice were considered positive if parasites were observed in any sample. To gauge the severity of the challenge, 4 groups of nave CD1 mice were challenged with 100, 33.3, 11.1 or 3.7 *P. yoelii* sporozoites. The results from these infectivity control mice indicated that the mice injected with 300 *P. yoelii* sporozoites were challenged with a dose equivalent to 7 times the $ID_{50}$ dose.

*P. yoellii* genes were cloned in a DNA and orthopox viruses, as above. The *P. yoelii* orthologous genes were cloned into plasmids for generating DNA vaccines. Poxvirus and adenovirus vectors expressing the *P. yoelii* orthologs were also generated. The DNA, poxvirus and adenovirus-

TABLE 1

| | Antigen ID # | *P. falciparum* Gene Locus | Screen Immune T cell | Screen Immune antibody | IFA Sporozoite Stage | IFA Liver Stage | IFA Blood Stage | *P. yoelii* Ortholog Locus | Individual Py Protection | Combined Py Protection |
|---|---|---|---|---|---|---|---|---|---|---|
| 1 | PF26 | PF11425w | Negative | Positive | Negative | Positive | Negative | PY00232 | ND | ND |
| 2 | PF56 | PF08_0008 | Positive | Positive | Positive | Positive | Positive | PY07130 | ND | ND |
| 3 | PF61 | PF10_0138 | Positive | Positive | Positive | Positive | Positive | PY04748 | ND | ND |
| 4 | PF106 | PFI0580c | Positive | Positive | Positive | Positive | Positive | PY03424 | 7% | 43% |
| 5 | PF116 | PFI0460w | Negative | Positive | Positive | Positive | Negative | PY03130 | ND | ND |
| 6 | PF121 | PF10_0319 | Positive | Positive | Positive | Positive | Positive | PY02600 | ND | ND |
| 7 | PF01 | PF10_0098 | ND | Positive | ND | ND | ND | PY04010 | ND | ND |
| 8 | PF08 | PFC0555c | ND | Positive | Positive | Pending | ND | PY03661 | 0% | 43% |
| 9 | PF09 | MAL7P1.32 | ND | Positive | ND | ND | ND | PY04689 | ND | ND |
| 10 | PF13 | PFC0700c | ND | Positive | ND | ND | ND | PY03459 | ND | ND |
| 11 | PF24 | PFC1055w | ND | Positive | ND | ND | ND | PY00359 | ND | ND |
| 12 | PF47 | PF11_0156 | ND | Positive | ND | ND | ND | PY02926 | ND | ND |
| 13 | PF51 | PFE0565w | ND | Positive | ND | ND | ND | PY00913 | ND | ND |
| 14 | PF59 | PF14_0495 | ND | Positive | ND | ND | ND | PY06813 | ND | ND |
| 15 | PF68 | PF14_0722 | ND | Positive | ND | ND | ND | PY00150 | ND | ND |
| 16 | PF72 | MAL13P1.25 | ND | Positive | NDd | ND | ND | PY05161 | ND | ND |
| 17 | PF93 | PF13_0012 | ND | Positive | ND | ND | ND | PY03011 | 7% | 43% |
| 18 | PF119 | PFD0235c | ND | Positive | Positive | Positive | Positive | PY01067 | ND | ND |
| 19 | PF78 | MAL8P1.78 | Positive | Positive | Positive | Positive | Negative | PY00566 | ND | ND |
| 20 | PF02 | PFE0785c | ND | Positive | Positive | Positive | Positive | PY00232 | 30% | ND |
| 21 | PF144 | PF14_0467 | Positive | Positive | Positive | Positive | Positive | PY05966 | ND | ND |
| 22 | PF131 | MAL13P1.107 | ND | Positive | ND | ND | ND | PY131 | ND | ND |

Example 4: Immunogenic Protection by *P. yoelii* Orthologous Genes

*P. yoelii* genes, listed in Table 1, that are orthologous to *P. falciparum* genes were evaluated for their ability to protect mice from challenge. For protection studies, CD1 mice were injected intramuscularly in the tibialis anterior muscle with 100 μl of vaccine (50 μl in each leg). The DNA vaccine vectors were prepared in 1× Phosphate Buffered Saline (PBS) and diluted to the appropriate concentration for vaccination in 1×PBS. The vaccinia vaccine vectors were prepared in 1 mM Tris (9.0) and diluted to the appropriate concentration for vaccination in 1×PBS. Mice were challenged intravenously in the tail vein with 300 *P. yoelii* (17XNL) sporozoites. Sp[orozoites were hand dissected from infected mosquito salivary glands and diluted for challenge in M199 medium containing 5% normal mouse serum.

In the first study, 14 mice per group were primed on day 0 with 100 μg of DNA-*P. yoelii* vaccine vector and boosted on day 40 with $5\times10^7$ plaque forming units (pfu) of vaccinia-based vaccine constructs were tested in mice using a prime-boost regimen and the mice challenged with *P. yoelii* sporozoites to assess protection.

In the second study, 14 mice per group were primed on day 0 with 100 μg of DNA-*P. yoelii* vaccine vector and 30 μg of DNA vector expressing murine granulocyte-macrophage colony-stimulating factor (mGM-CSF) and boosted on day 42 with $3.3\times10^7$ pfu of vaccinia-*P. yoelii* vaccine vector. Mice immunized with 2 or 3 DNA-*P. yoelii* vectors were primed with a total of 200 μg or 300 μg of the DNA-*P. yoelii* vectors and 30 μg of the DNA-mGM-CSF vector and boosted with a total of $6.6\times10^7$ pfu or $1\times10^8$ pfu of the vaccinia-*P. yoelii* vectors, respectively. Three separate groups fo the negative control mice were immunized with 3 different doses o the DNA and vaccinia vectors that do not express a *P. yoelii* antigen. One group was primed with 100 μg of an "empty" DNA vector and 30 μg of a DNA-mGM-CSF vector and boosted with $3.3\times10^7$ pfu of an "empty" vaccinia vector. A second group was primed with 200 μg of an "empty" DNA vector and 30 μg of a DNA-mGM-CSF vector and boosted with $6.6\times10^7$ pfu of an "empty" vaccinia vector. A third group was primed with 300 μg of an "empty" DNA vector and 30 μg of a DNA-mGM-CSF vector and boosted with $1\times10^8$ pfu of an "empty" vaccinia vector. On day 52, the mice were bled and sera prepared. On day 57, the mice were challenged with 300 *P. yoelii* sporozoites. On days 64-71, parasitemia was evaluated by visualization of Giemsa-stained blood smears. Mice were considered positive if parasites were observed in any sample. To gauge the severity of this challenge, 4 groups of naïve mice were challenged with 100, 33.3, 11.1 or 3.7 *P. yoelii* sporozoites. The results from these infectivity control mice indicated that the mice injected with 300 *P. yoelii* sporozoites were challenged with a dose equivalent to 13.6 times the $ID_{50}$ dose.

It should be noted that the regimens for the two protection studies were slightly different. For example, the dose of the individual vaccinia-*P. yoelii* vectors was slightly higher in protection study one ($5\times10^7$ pfu) than protection study 2 ($3.3\times10^7$ pfu). Consequently, the total dose of the trivalent vaccine was $1.5\times10^8$ pfu in protection study one and $1\times10^8$ pfu in protection study two. Additionally, in protection study 2, the DNA vectors were mixed with a DNA-mGM-CSF plasmid. Although previous studies had indicated that co-administration of a DNA-PyCSP vector with the DNA-mGM-CSF plasmid could enhance the immunogenicity and efficacy of a DNA-vaccinia prime-boost regimen, the DNA-mGM-CSF plasmid did not appear to enhance the efficacy of the PyCSP or trivalent *P. yoelii* vaccines in protection study two, relative to one.

As illustrated in Table 1 and FIG. 1 (panel A), none of the 14 mice immunized with vectors that express PY03011 or PY03661 were sterilely protected (i.e., 0% protection). Additionally, 2 out of 14 mice immunized with PY03424 were protected (i.e., 14%). However, when all three antigens were used (i.e., PY03011; PY03424 and PY03661), 57% protection was observed. This was greater than that seen with PyCSP.

The results of a second study, FIG. 1 (panel B) and Table 1, further confirmed that additive protective effect of the *P. yoelii* polypeptides. As illustrated in Table 1 and in FIG. 1 (panel B), none of the mice immunized with vectors that express PY03661 were protected and only 1 of 14 mice immunized with vectors that express PY03011 or PY03424 were protected (7% protection). However, 6 of 14 mice immunized with PY03011 and PY03424 were protected (i.e., 43%), 3 of 14 mice immunized with PY03424 and PY03661 were protected (i.e., 21% protection) and 6 of 14 mice immunized with all 3 *P. yoelii* antigens were protected (i.e., 43% protection). The protection elicited by PY03011 and PY03424 in this study is statistically significant (PY03011/PY03424 (dose=2× vs Neg control (dose=2×), p=0.0159). Similar to the previous study, the protection elicited by the combination of PY03011 and PY03424 or all 3 antigens was greater than the protection elicited by PyCSP (i.e., 43% vs. 14%).

Figure 2:
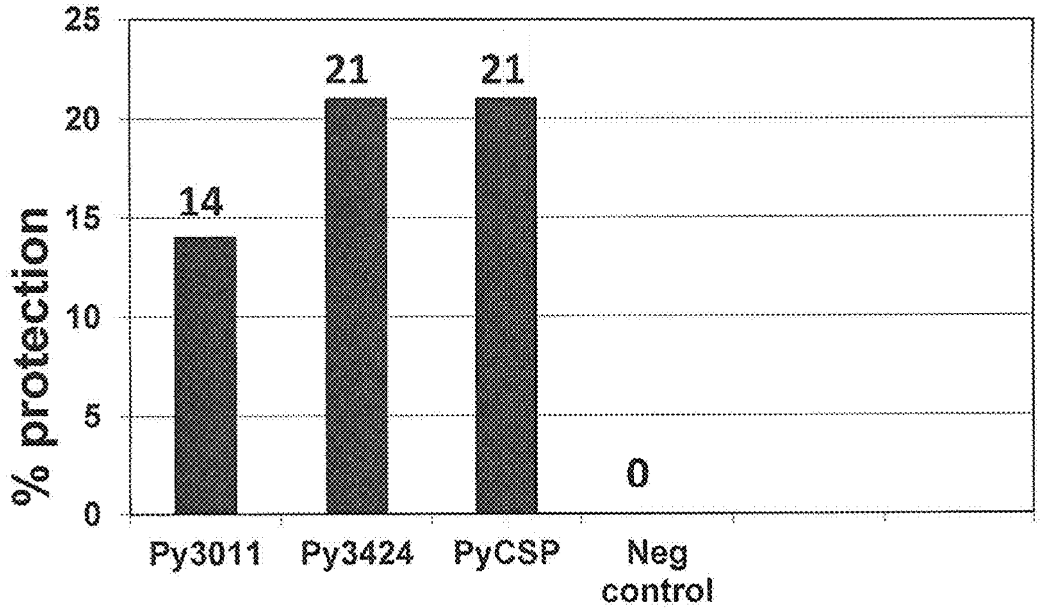
FIG. 2. Protection of mice immunized as in FIG. 1. In these studies, N=14. Mice receiving more than one insert are indicated as receiving multiple doses (i.e., dose=1× or 3×).

In another study, FIG. 2, 14 CD1 mice were again immunized using a DNA/adenovirus prime boost regime. In this study, a greater response was observed using PY3011 or PY3424, singly. In fact, the response to PY3424 was equivalent to that observed for PYCSP. A third antigen, PY4748 resulted in 1 out of 14 mice were protected. Interestingly, when all three antigens (i.e., PY3011, PY3424 and PY4748) were used to immunize CD1 mice, no protection was observed. The causation of this result is not clear.

The results of this study illustrate the potential value of *P. yoelii* proteins in conferring immunity against *P. yoelii*. Of interest is that the additive effect of the proteins resulted in protection often beyond that which would have been predicted from mice immunized with only a single protein. For example, in FIG. 1, panel A, PY03011 or PY03661 did not result in protection. Similarly, immunization with PY03424 resulted in only 14% protection. However, immunization of the genes in combination, albeit at a higher dose due to all three being administered simultaneously, resulted in protection higher than PyCSP.

From these analyses, the orthologous *P. falciparum* genes would be important candidates to be included in compositions for the induction of immunity against malaria. The *P. falciparum* orthologs are listed in Table 1. For all of these *P. yoelii* gene products tested in these murine protection studies, the *P. falciparum* orthologs reacted positively to either immune human serum and/or T-cell. A summary of the DNA and protein sequences are summarized in Table 2.

TABLE 2

| SEQ ID No. | Clone | Gene Name | Protein or DNA |
|---|---|---|---|
| SEQ 1 | PF56 | PF08_0008 | DNA |
| SEQ 2 | PF56 | PF08_0008 | protein |
| SEQ 3 | PF61 | PF10_0138 | DNA |
| SEQ 4 | PF61 | PF10_0138 | protein |
| SEQ 5 | PF106 | PFI0580c | DNA |
| SEQ 6 | PF106 | PFI0580c | protein |
| SEQ 7 | PF121 | PF10_0319 | DNA |
| SEQ 8 | PF121 | PF10_0319 | protein |
| SEQ 9 | PF08 | PFC0555c | DNA |
| SEQ 10 | PF08 | PFC0555c | protein |
| SEQ 11 | PF144 | PF14_0467 | DNA |
| SEQ 12 | PF144 | PF14_0467 | Protein |
| SEQ 13 | PF93 | PF13_0012 | DNA |
| SEQ 14 | PF93 | PF13_0012 | Protein |

Example 5: Immune Recognition of *P. falciparum* Genes Orthologous to *P. yoelii*

Figure 3:
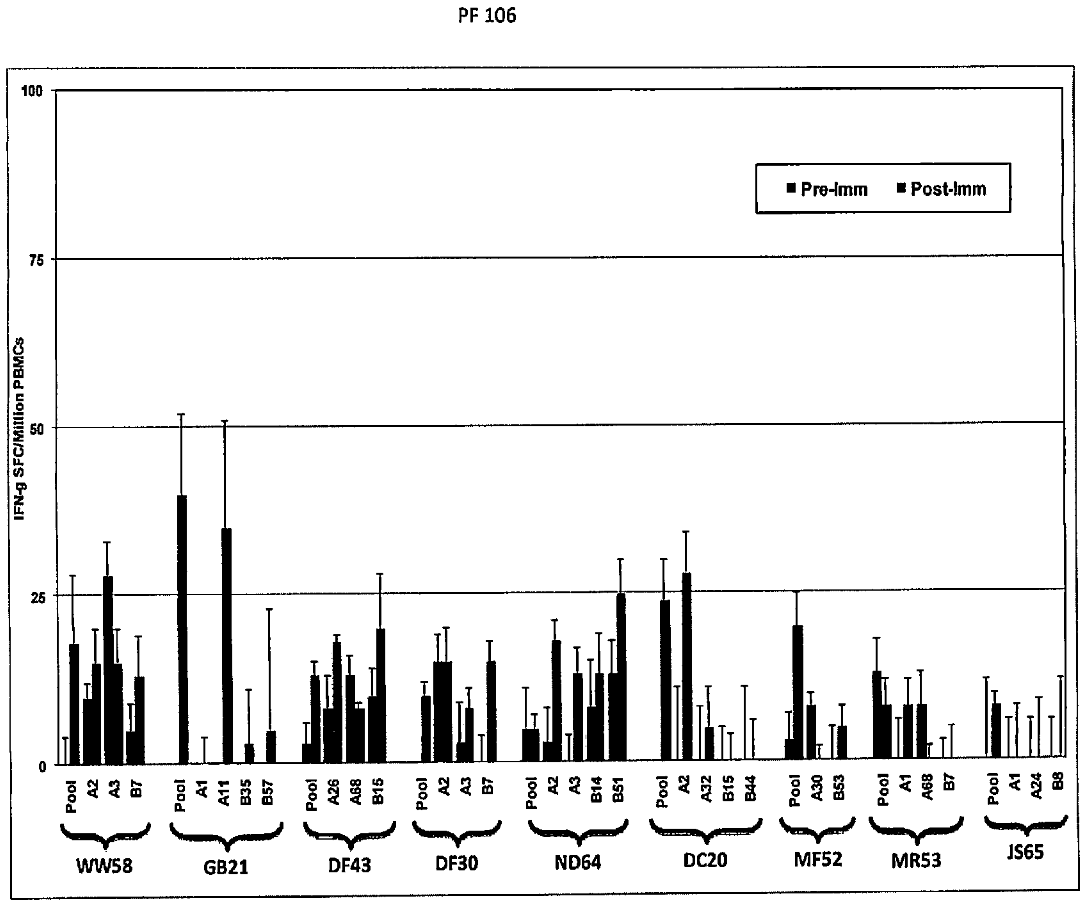
FIG. 3. ELISpot screening of PF106 antigen using HLA-specific peptide pools as stimulants (IFN-γ spot-forming cells (SFC)/million peripheral blood mononuclear cells (PBMC)). A star indicates the highest IFN-γ induction.
Figure 4:
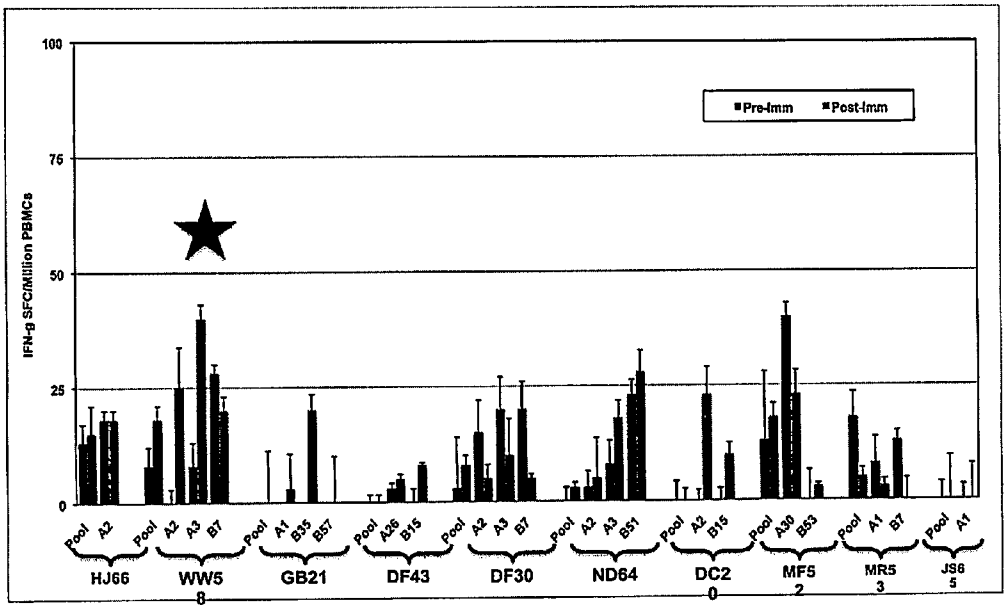
FIG. 4. ELISpot screening of PF 61 antigen using HLA-specific peptide pools as stimulants (IFN-γ spot-forming cells (SFC)/million PBMC). A star indicates the highest IFN-γ induction.
Figure 5:
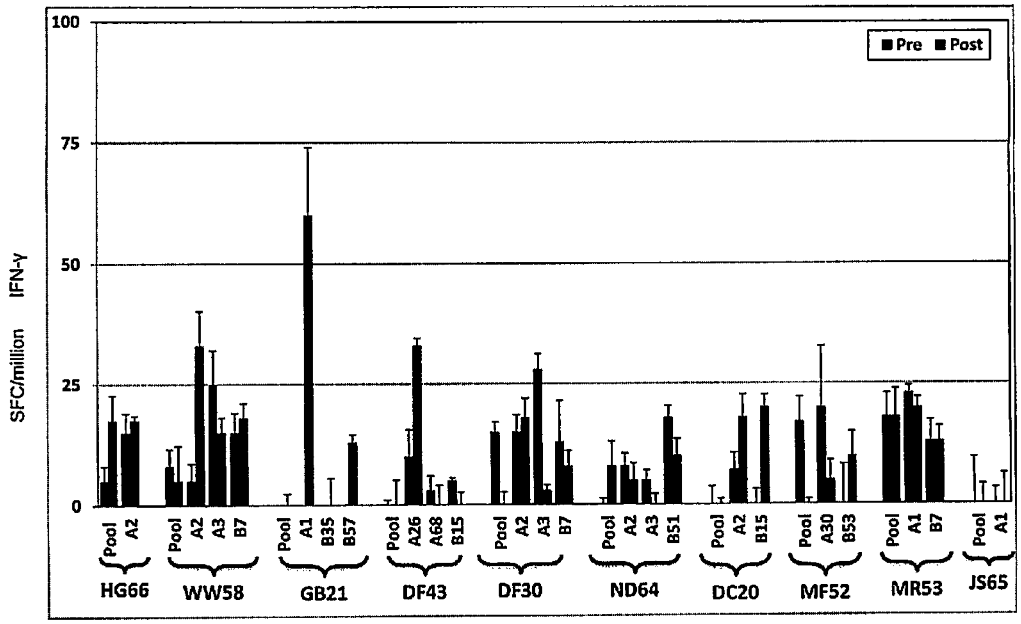
FIG. 5. ELISpot screening of PF 56 antigen using HLA-specific peptide pools as stimulants (IFN-γ spot-forming cells (SFC)/million PBMC). A star indicates the highest IFN-γ induction.
Figure 6:
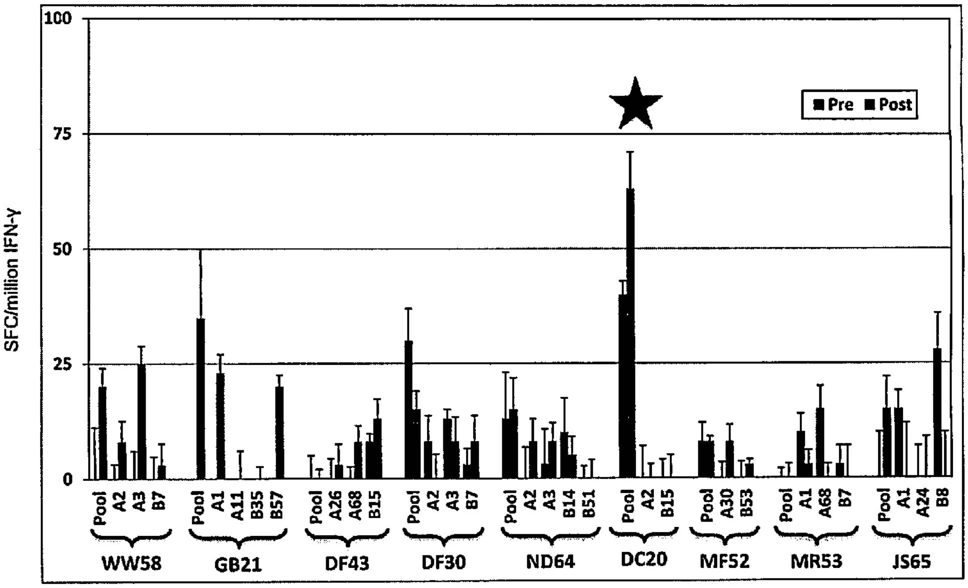
FIG. 6. ELISpot screening of PF 121 antigen using HLA-specific peptide pools as stimulants (IFN-γ spot-forming cells (SFC)/million PBMC). A star indicates the highest IFN-γ induction.

From the *P. yoelii* protection data, orthologous *P. falciparum* genes were identified and further evaluated for their ability to confer cellular immunity. Illustrated in FIG. 3 are the results of utilizing the *P. falciparum* ortholog to PY3424, PF 106, as an antigen in inducing a T-cell response, as evidenced by its ability to induce IFN-γ in PBMCs in ELISpot assays. The results are presented in spot-forming cells (SPC)/million.

In FIG. 3, the "pool" represents 15-mer peptides, overlapping by 10-mers, encompassing the entire length of the PF 106 protein. Additionally, HLA class I-specific 15-mer peptide pools were developed and also used as antigen. The HLA class I-specific pools contained 12 to 15 peptides, each containing an HLA class I binding motifs for specific HLA class I alleles. The HLA genotypes of the PBMCs are summarized in Table 3. All volunteers had been immunized with ISV, with some exhibiting a protective immune response. The results of these studies are illustrated in FIG. 3.

TABLE 3

| Volunteer | Sex | Age | HLA-A | HLA-B | HLA DR | Cohort |
|---|---|---|---|---|---|---|
| DF0043 | Male | 37 | A26, A'68 | B15, B38/39 | DRB1*13, DRB3*02/03 | Not protected |
| MF0052 | Male | 39 | A3002, A'3402 | B'53, B0812 | DRB1*03/06/11, DRB3*02/03 | Not protected |
| MR0053 | Male | 45 | A1, A'6802 | B7, B18 | DRB1*1503, DRB1*07MT, DRB4*01, DRB5BFK | Not protected |
| JS0065 | Male | 26 | A1, A'24 | B8, B44 | DRB1*13, DRB1*08DKZ, DRB3*01 | Not protected |
| DC0020 | Male | 41 | A2, A'32 | B15, B'44 | DRB1*04BMS, DRB1*14APF, DRB3*02CAY | Not protected |
| GB0021 | Male | 29 | A1, A11 | B35, B57 | DRB1*01AD, DRB1*07AC | Protected |
| DF0030 | Male | 47 | A2, A3 | B7, B40DGE | DRB1*01AD, DRB1.2 03YH, DRB3.1 01MN | Protected |
| WW0058 | Male | 32 | A2, A'3 | B7, B44 | DRB1*02, DRB5*01/02 | Protected |
| ND0064 | Male | 21 | A2, A'3 | B14, B'51 | DRB1*02, DRB1*03/06, DRB3*02/03, DRB5*01BFK | Protected |
| HG0066 | Male | 38 | A2, A'2 | B18, B39 | DRB1*08/14/(03), DRB3*02/03 | Protected |

As illustrated in FIG. 3, the peptide pool generally induced a significant T-cell response with a greater response in PBMC's from immunized volunteers, compared to pre-immunized PBMC. Post-immune PBMC's from several individuals, e.g., GB21; DF0030, showed relatively high induction of IFN-γ. In fact, the volunteer GB21 exhibited a protective immune response against malaria. Additionally, peptide antigens containing HLA class I binding motifs generally resulted in significant IFN-γ induction. Interestingly, PBMCs from GB21, which gave the overall greatest IFN-γ induction, yielded a level of IFN-γ SPC, using A11 HLA pools as antigen, equivalent to that observed with the pool of 15-mers. This suggests that PF106 not only contains anti-*P. falciparum* epitopes but that some epitopes may be important in immunity against malaria. Furthermore, regions of PF106 operate in an HLA-restricted fashion to induce class I T-cell immunity.

In addition to PF106, other *P. falciparum* proteins were utilized as antigens in IFN-γ ELISpot assays resulted in HLA class I specific induction of IFN-γ. These include PF61, PF56, PF121 and PF144. The results of these studies are illustrated in FIGS. 3-7, respectively. Additionally, the results are summarized in Table 1. The DNA and protein sequence identification numbers are summarized in Table 2.

Figure 7:
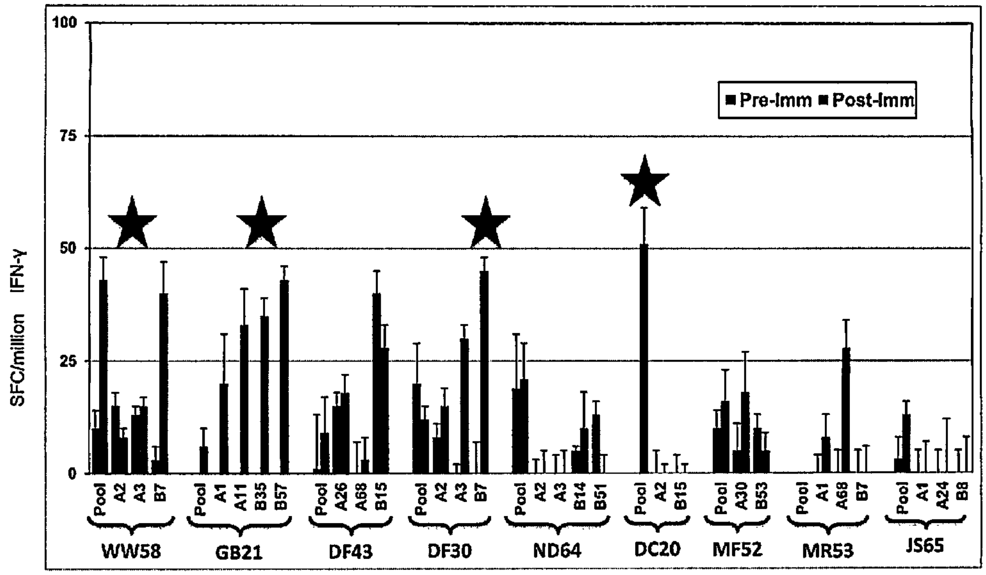
FIG. 7. ELISpot screening of PF 144 antigen using HLA-specific peptide pools as stimulants (IFN-γ spot-forming cells (SFC)/million PBMC). A star indicates the highest IFN-γ induction.

The T-cell response elicited by PF144 was particularly noteworthy. As shown in FIG. 7, PBMC's from four individuals, exposed to PF144, resulted in a high level of IFN-γ secreting cells. Of note is that three of the four individuals were previously shown to have elicited a protective immune responses against malaria, suggesting the importance of this protein in protection. Furthermore, peptides containing HLA binding motifs to class I alleles induced an IFN-γ response, in some cases, such as in GB21, WW58 and DF30, equivalent or even greater than that observed when the pool of 15-mer peptides twere used.

Figure 8:
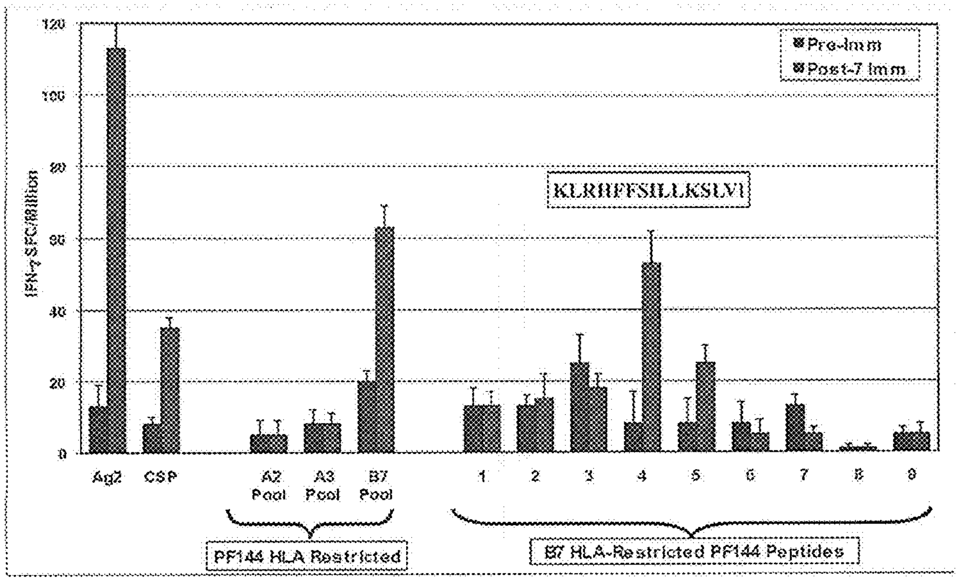
FIG. 8. ELISpot screening of PF 144 antigen using HLA-restricted (A2, A3 and B7) peptide pools as stimulants (IFN-γ spot-forming cells (SFC)/million PBMC). PBMC's were obtained from a subject pre- or post-immunization with irradiated sporozoite vaccine (ISV).

In furtherance to the notion that PF144 contains T-cell epitopes important in conferring immunity against malaria, polypeptide containing motifs associated with B7 were analyzed in greater detail for their ability to induce IFN-γ. As illustrated in FIG. 8, the IFN-γ responses to peptide pools were analyzed in PBMCs from WW58. As seen in FIG. 8, the results using A2 and A3 pools were consistent to that illustrated in FIG. 7. However, in using B7 pools as antigen, one peptide in particular, KLRHFFSILLKSLVI, containing a B7 binding motif, induced a high IFN-γ response in the immune PBMCs. This suggests the likely importance of B7 allele in class I T-cell immunity against PF144.

The data in FIG. 1-8 strongly suggest that the protein antigens PF106, 61, 56, 121 and 144 contain epitopes important in conferring protection against *P. falciparum* malaria. Furthermore, the proteins are able to induce class I specific responses, as evidenced by their ability to induce a T-cell response to antigen containing specific HLA class I peptide binding motifs.

Example 6: Incorporation Into Expression Systems

This example illustrates prophetic uses of the recombinant genes encoding the novel antigens by incorporating one or more of the antigens of Table 2, or nucleic acid encoding the antigens into vaccine formulations. Alternatively, immunogenic fragments of the antigens or derivatives of the antigens of Table 2 can be utilized. It is contemplated that the antigens can be expressed either as a component of a DNA vaccine or other platform system. An example of a contemplated expression system includes, but is not limited to, viral systems, including replicating and nonreplicating vectors. Examples of contemplated viral vectors include adenvirus, alphavirus, posvirus, cytopmegalovirus, canine distemper virus and yellow fever virus. The antigen could be incorporated as an insert of a DNA or other vaccine expression system, either as a single antigen or multiple antigen expression systems from a single or multiple promoters.

The contemplated invention includes a method for inducing an immune response in mammals, including humans. In this example, antigens, either as polypeptide or incorporated into a nucleic acid expression system, such as a DNA or viral system, are administered in one or more doses. The method also contemplates inducing an immune response utilizing a prime-boost immunization regimen. In this embodiment, one or more priming immunization doses would be administered followed by one or more boosting immunizations.

The priming and boosting immunization comprises a composition containing one or more malaria polypeptides, wherein the polypeptides contains the amino acid sequence of SEQ ID Nos. 2, 4, 6, 8, 10, 12 or 14, or immunogenic derivatives, thereof. Alternatively, the immunogenic composition can be comprised of an expression system capable of expressing the polypeptides. In this embodiment, nucleic acid molecules, encoding these polypeptides, with the nucleic acid sequences of SEQ ID Nos. 1, 3, 5, 7, 9, 11 or 13, can be inserted into a DNA plasmid or a viral expression vector. Examples of viral expression vector systems include: alphavirus (and alphavirus replicons), adenovirus, poxvirus, adeno-associated virus, cytomegalovirus, canine distemper virus, yellow fever virus and retrovirus.

The contemplated methods include immunization regimens wherein the priming immunization comprises malarial peptides expressed from a DNA plasmid expression vector or an adenovirus, while the boosting immunization includes malaria peptides expressed from either: adenovirus, adenovirus that is heterologous to the priming adenovirus, poxvirus or one or more malaria polypeptides. The malaria polypeptides include polypeptides with the amino acid sequences of SEQ ID NO. 2, 4, 6, 8, 10, 12 or 14, or immunogenic derivatives, thereof.

All references, including publications, patent applications and patents, cited herein are hereby incorporated by reference.

Having described the invention, one of skill in the art will appreciate in the appended claims that many modifications and variations of the present invention are possible in light of the above teachings. It is therefore, to be understood that, within the scope of the appended claims, the invention may be practiced otherwise than as specifically described.

What is claimed is:

1. An immunogenic composition comprising a vector expression system, wherein said vector comprises nucleic acid sequences encoding separate polypeptides wherein the separate polypeptides comprise a polypeptide with the amino acid sequence of SEQ ID NOs: 6 and a polypeptide comprising the amino acid sequence of SEQ ID NO. 10, wherein said suitable vector expression system is a DNA plasmid or replicating or nonreplicating viral vector.

2. The immunogenic composition of claim 1, wherein said separate polypeptides are encoded by the nucleic acid sequences of SEQ ID NOs. 5 or 9 inserted into said suitable vector expression system.

3. A method of inducing an immune response against malaria in a mammal, which method comprises administering the immunogenic composition of claim 1.

4. The method of claim 3, wherein of said isolated polypeptides are encoded by the nucleic acid sequences of SEQ ID NOs. 5, or 9.

5. The method of claim 3, wherein said method further comprises administering to said mammal one or more priming and one or more boosting immunizations, wherein said priming and boosting immunizations of an immunologically effective amount of said polypeptides of claim 1 expressed by a suitable plasmid or replicating or nonreplicating viral vector.

6. The method of claim 5, wherein said suitable expression vector is selected from the group consisting of DNA plasmid, alphavirus replicon, adenovirus, poxvirus, adeno-associated virus, cytomegalovirus, canine distemper virus, yellow fever virus, retrovirus, RNA replicons, DNA replicons, alpha virus replicon particles, Venzuelean Equine Encephalitis Virus, Semliki Forest Virus and Sindbus Virus.

7. The method of claim 6, wherein the poxvirus is selected from the group consisting of cowpox, canarypox, vaccinia, modified vaccinia Ankara, or fowlpox.

8. The immunogenic composition of claim 1, wherein said vector expression system also comprises nucleic acid sequence of SEQ ID NO. 13 encoding the polypeptide with the amino acid sequence of SEQ ID NO. 14.

9. The immunogenic composition of claim 1 or claim 8, wherein said vector expression system also comprises nucleic acid sequence encoding one or more of the polypeptides with the amino acid sequences selected from the group consisting of SEQ ID NOs: 2, 4, 8, and 12.

10. The immunogenic composition of claim 9, wherein said nucleic acid sequences are selected from the group consisting of SEQ ID NOs: 1, 3, 7, and 13.

11. The method of claim 3, wherein said composition also comprises nucleic acid sequences encoding one or more of the polypeptides with the amino acid sequence selected from the group consisting of SEQ ID NOs. 2, 4, 8, 12 and 14.

12. The method of claim 11, wherein said nucleic acid sequences are selected from the group consisting of SEQ ID NOs. 1, 3, 7 and 13.

* * * * *

SEQUENCE LISTING

```
<160> NUMBER OF SEQ ID NOS: 14

<210> SEQ ID NO 1
<211> LENGTH: 2217
<212> TYPE: DNA
<213> ORGANISM: Plasmodium falciparum

<400> SEQUENCE: 1

atgaaatatt atacatcttt gtacgttgca cttataatag ccttatgtca ggcggtaagt     60

gcccttataa gaaattcgaa cactcctcag gccttcttaa tacctgaatt gaataataat    120

gaaaaaaacg aatttaataa taatgaaaaa aacgaaatga ataataattt aaataacgaa    180

tttaataata atgaagaaaa ttgtgatata caaaaaatag cagaagaaat gatggagaat    240

ttattgaatg aaaatgatat gtatactaat ataatgttat cattacaaaa tagattaagt    300

gatgattatt tatgctcaga gccaaaatat gagaatatat gtatacatga aaaagataaa    360

atttctttat cctttccttg ttcaaatcct aaatatgaaa aattaataca taaattcaca    420

tttaaaaaat tatgtaactc caaagcagct tttaataata ctttacttaa atcttttatt    480

gaggaagatg aagaacaaaa tacatttagt cttatgttaa aacaatttaa aatattatta    540

acatgtgtgg atgacgaatt aaaagatata tataaagaat ctattgattt attagtcgat    600

ttaaaaacat ccattactga attaacacaa aaattatggt caggtaaaat ggttaatgtt    660

ttaaaaaaaa gagaattctt aataactggt attttgtgtg aattaaggaa tggtaataag    720

tcaccactta ttagtaaaag tttagaattt gaaaatctgg gaatattaaa aatgaataat    780

gaagaattat taaatgaagc ttataatgcc ttttcagatt attattattt ttttccatat    840

tttattcaaa aattattaga aaagggtgga atgatagaaa ggttaattaa aattcatgaa    900

aacttgacta aatatagaac aaaagatatg gtaaataaaa ttaatgcaca atcaaaagga    960

gaagtattaa ataatgaaga tatacttaat aaactaaatg catataagca ttatacaaag   1020

catggtgcaa cttcatttat ccaatctagg gaagtaaaaa ttgtgaacca aaacgtaaac   1080

aatgacgaca ccacaaaaaa tcagcaacaa aatgttaata ataatgaaaa attaaataat   1140

aataataata ataataataa tcaacaagta aataataata ataataataa taatcaacaa   1200

gtaaataata ataataataa taataataac caagtaaata ataataataa taataataat   1260

aaccaagtaa ataacaataa ttataataat aataaccaag taaataacaa taataataat   1320

aaccaacaag taaataataa taataattat aataaccaac taaataacaa taattttaat   1380

aataacctac aggtaaataa aaacgataaa catgtaccaa aaaacaacca cacaactgca   1440

acacacacaa ataatatttt gtacaatcct ttatattcca tcaatccaga aaaaccaaag   1500

gatattataa aattattaaa agatttaata aaatatttac atattgttaa atttgaaaat   1560

aatgaaccta ccacaaacat tgatgaagaa ggaattagaa aacttttgga aaatagtttt   1620
```

-continued

```
tttgatttga atgatgatat tcttatagtc cgtttattac taaaaccaca aacagtaata   1680

ttaacggtca tacaatcctt tatgctaatg accccttccc catcaagaga tgcaaaagct   1740

tattgtaaga aggcattaat taatgatcaa ttagtaccaa ctaatgatac taatattttg   1800

tcagaagaaa atgaattagt taataacttc tctacgaaat atgttttgat atatgaaaaa   1860

atgaaattac aagaattaaa agaaatggaa gaaagcaaat taaaaatgaa atattctaaa   1920

accaatttat cagctttaca agttacaaat ccacaaaaca ataaagacaa aaatgatgca   1980

tccaataaaa ataataaccc aaataatagt agtacaccat taattgctgt agtaacagat   2040

ttatctggtg aaaaaacaga agatataata aataataatg tcgacatagc tacattatca   2100

gttggggtac aaaatacttt tcaaggacca aatgcaaagg caggaagttt aattaatcac   2160

ctctcttatg caacattcct tttttttcg ttcattttaa ttaacttgtt aaattaa        2217
```

```
<210> SEQ ID NO 2
<211> LENGTH: 738
<212> TYPE: PRT
<213> ORGANISM: Plasmodium falciparum

<400> SEQUENCE: 2

Met Lys Tyr Tyr Thr Ser Leu Tyr Val Ala Leu Ile Ile Ala Leu Cys
1               5                   10                  15

Gln Ala Val Ser Ala Leu Ile Arg Asn Ser Asn Thr Pro Gln Ala Phe
            20                  25                  30

Leu Ile Pro Glu Leu Asn Asn Asn Glu Lys Asn Glu Phe Asn Asn Asn
        35                  40                  45

Glu Lys Asn Glu Met Asn Asn Asn Leu Asn Asn Glu Phe Asn Asn Asn
    50                  55                  60

Glu Glu Asn Cys Asp Ile Gln Lys Ile Ala Glu Glu Met Met Glu Asn
65                  70                  75                  80

Leu Leu Asn Glu Asn Asp Met Tyr Thr Asn Ile Met Leu Ser Leu Gln
                85                  90                  95

Asn Arg Leu Ser Asp Asp Tyr Leu Cys Ser Glu Pro Lys Tyr Glu Asn
            100                 105                 110

Ile Cys Ile His Glu Lys Asp Lys Ile Ser Leu Ser Phe Pro Cys Ser
        115                 120                 125

Asn Pro Lys Tyr Glu Lys Leu Ile His Lys Phe Thr Phe Lys Lys Leu
    130                 135                 140

Cys Asn Ser Lys Ala Ala Phe Asn Asn Thr Leu Leu Lys Ser Phe Ile
145                 150                 155                 160

Glu Glu Asp Glu Glu Gln Asn Thr Phe Ser Leu Met Leu Lys Gln Phe
                165                 170                 175

Lys Ile Leu Leu Thr Cys Val Asp Asp Glu Leu Lys Asp Ile Tyr Lys
            180                 185                 190

Glu Ser Ile Asp Leu Leu Val Asp Leu Lys Thr Ser Ile Thr Glu Leu
        195                 200                 205

Thr Gln Lys Leu Trp Ser Gly Lys Met Val Asn Val Leu Lys Lys Arg
    210                 215                 220

Glu Phe Leu Ile Thr Gly Ile Leu Cys Glu Leu Arg Asn Gly Asn Lys
225                 230                 235                 240

Ser Pro Leu Ile Ser Lys Ser Leu Glu Phe Glu Asn Leu Gly Ile Leu
                245                 250                 255

Lys Met Asn Asn Glu Glu Leu Leu Asn Glu Ala Tyr Asn Ala Phe Ser
            260                 265                 270
```

-continued

```
Asp Tyr Tyr Tyr Phe Phe Pro Tyr Phe Ile Gln Lys Leu Leu Glu Lys
        275                 280                 285

Gly Gly Met Ile Glu Arg Leu Ile Lys Ile His Glu Asn Leu Thr Lys
    290                 295                 300

Tyr Arg Thr Lys Asp Met Val Asn Lys Ile Asn Ala Gln Ser Lys Gly
305                 310                 315                 320

Glu Val Leu Asn Asn Glu Asp Ile Leu Asn Lys Leu Asn Ala Tyr Lys
                325                 330                 335

His Tyr Thr Lys His Gly Ala Thr Ser Phe Ile Gln Ser Arg Glu Val
            340                 345                 350

Lys Ile Val Asn Gln Asn Val Asn Asn Asp Asp Thr Thr Lys Asn Gln
        355                 360                 365

Gln Gln Asn Val Asn Asn Asn Glu Lys Leu Asn Asn Asn Asn Asn Asn
    370                 375                 380

Asn Asn Asn Gln Gln Val Asn Asn Asn Asn Asn Asn Asn Asn Gln Gln
385                 390                 395                 400

Val Asn Asn Asn Asn Asn Asn Asn Asn Asn Gln Val Asn Asn Asn Asn
                405                 410                 415

Asn Asn Asn Asn Asn Gln Val Asn Asn Asn Asn Tyr Asn Asn Asn Asn
            420                 425                 430

Gln Val Asn Asn Asn Asn Asn Asn Asn Gln Gln Val Asn Asn Asn Asn
        435                 440                 445

Asn Tyr Asn Asn Gln Leu Asn Asn Asn Asn Phe Asn Asn Asn Leu Gln
    450                 455                 460

Val Asn Lys Asn Asp Lys His Val Pro Lys Asn Asn His Thr Thr Ala
465                 470                 475                 480

Thr His Thr Asn Asn Ile Leu Tyr Asn Pro Leu Tyr Ser Ile Asn Pro
                485                 490                 495

Glu Lys Pro Lys Asp Ile Ile Lys Leu Leu Lys Asp Leu Ile Lys Tyr
            500                 505                 510

Leu His Ile Val Lys Phe Glu Asn Asn Glu Pro Thr Thr Asn Ile Asp
        515                 520                 525

Glu Glu Gly Ile Arg Lys Leu Leu Glu Asn Ser Phe Phe Asp Leu Asn
    530                 535                 540

Asp Asp Ile Leu Ile Val Arg Leu Leu Leu Lys Pro Gln Thr Val Ile
545                 550                 555                 560

Leu Thr Val Ile Gln Ser Phe Met Leu Met Thr Pro Ser Pro Ser Arg
                565                 570                 575

Asp Ala Lys Ala Tyr Cys Lys Lys Ala Leu Ile Asn Asp Gln Leu Val
            580                 585                 590

Pro Thr Asn Asp Thr Asn Ile Leu Ser Glu Glu Asn Glu Leu Val Asn
        595                 600                 605

Asn Phe Ser Thr Lys Tyr Val Leu Ile Tyr Glu Lys Met Lys Leu Gln
    610                 615                 620

Glu Leu Lys Glu Met Glu Glu Ser Lys Leu Lys Met Lys Tyr Ser Lys
625                 630                 635                 640

Thr Asn Leu Ser Ala Leu Gln Val Thr Asn Pro Gln Asn Asn Lys Asp
                645                 650                 655

Lys Asn Asp Ala Ser Asn Lys Asn Asn Asn Pro Asn Asn Ser Ser Thr
            660                 665                 670

Pro Leu Ile Ala Val Val Thr Asp Leu Ser Gly Glu Lys Thr Glu Asp
        675                 680                 685
```

-continued

```
Ile Ile Asn Asn Asn Val Asp Ile Ala Thr Leu Ser Val Gly Val Gln
    690                 695                 700

Asn Thr Phe Gln Gly Pro Asn Ala Lys Ala Gly Ser Leu Ile Asn His
705                 710                 715                 720

Leu Ser Tyr Ala Thr Phe Leu Phe Phe Ser Phe Ile Leu Ile Asn Leu
                725                 730                 735

Leu Asn
```

<210> SEQ ID NO 3
<211> LENGTH: 4368
<212> TYPE: DNA
<213> ORGANISM: Plasmodium falciparum

<400> SEQUENCE: 3

```
atgaatcgaa tattttattt ttgtttgttt actattttgt tttggttatc tcttgtatct     60

ggtgaaaatg ttaataataa aaactgtaat gagaaaaata ggaaagctat tttattagct    120

ttattaaaaa attcattagt agataataag gattataaca atagtgaaga attaaagtat    180

gcattggaac atatccagaa ttctgaatta tatccaaagg attcgaaaaa atttgacaaa    240

tttattgatg aattttttag ttattataat attcatgtaa attttactga tgaagaaaaa    300

agaatattac atatatcagg tgtcttcaaa gaattttatg tagatgtaga taatttaaat    360

aaagatgaaa tgaaagaata ttttaagaaa aattatgaaa aaggtctttc tttaattaat    420

ttaatagttc atagtaattt aataattcaa caatttgatc atgatattat agataaaaaa    480

aaagtacatg aacaaaacac aaatacaaat aaaactttag aatatatatc tgataattta    540

aatgatctaa ttaatttcaa aaatattcat ttaaataata attccactgg agattttatt    600

atcaaattat atacaaatta tgtgaattat attaaccctt atcaaacaaa ccctttgcca    660

aatacacccc actattacga acataaaaat tttcatacga aagaacatta tatatacgac    720

gaggaaatag ttaatccaaa tatggataat ataaatacac acactgaaga ggataatgtg    780

tatgtatcag ctacaaaagg aaatcaaaaa gaagaaactg aaaaaaaaga aaatcatgaa    840

aataataatg caattaatcc taaatatatg aattatgaaa catattataa aaaaatattc    900

aatgccatat ttgaacaaat agataaacta aataaaacac tttttgaaat taaaaataaa    960

aataacagtg aaacaaatga aaatatttct gaatcaaatt ctggaaatcc agaattaaac   1020

aatgaaaata gctattctgt aaaattgtcc agttcgtcac ccaattcaac taacaaagaa   1080

tctttaatct ttccatatac ttattacaat ccatattata tgttcagatt aactaataat   1140

tttaaagaaa atgatgaagg tttaaaaaat gaaaacaata tcaacaataa tgaagataac   1200

caaaatgata atatgaacat agttttgggg aaaatacata atattttaaa agattttaat   1260

attaatgaaa atattatgac taataaaatg tcagcaccac ttataatgac aatcatttta   1320

aattttttca aaaaatatat ggctgaaaat aaatttaatc ttccaatgtc atcagaggtt   1380

gaaaataaaa ttaacaaatc caataataaa gcattattac aacaaagtaa taaagataca   1440

ccaatacata aaaaaaaaga aattagaaat aaaaaaatac aaacaaaagt agacgtaatt   1500

gatgaaaaga caaaaaaaaa aattgcaaat actatttatg taaatgttgg acaaagtggt   1560

attaatggat tttttaattt ttttgatttt agagaaaaat ctatagatag caatatcttt   1620

gatttgttac atgtaatgga agatatgaaa atatttgata ttttccaaac tattatattt   1680

attcaaaaat ttacagaaaa tgtatgtgca tcttattgta tgaatattac cgatgtgcta   1740

gaattatcac actatgatat gatattttat gataaaatgg ttttccattt tagtaaggat   1800
```

-continued

```
ggaatgatga taaagacgga taaaaaatat ttatataatt taaaagaatt tgaaaatata   1860
cttaatttat taaatataaa tgctaatacc atagcattaa attgtacttg taaattttat   1920
gtagacgtta attatacata ttctgaacaa tataaaatgc atttaaaagg atatctccat   1980
aaaatgaatg aatttgatta tattaataat ttttcagcat cgtatctttt aaatcaatta   2040
ataattttcc aagataaatt taattatatt aaaatgaatg gaaaactacc tattgatgat   2100
ccaaaaaata tatataatat gaataatgta cacgatacag catattatca taattctaga   2160
tatttcccaa ccaaagatat gccaagttta gaagacaatt tttatgaaca ccttaaatat   2220
cctgatataa atactattca tatttattat aatgcttccc cagttaaatt aaatgaagtg   2280
aatgatttaa aaactataat tattgatgaa ataaaatcga aaattttcta tattaattct   2340
tatagagtag gagatcaatt tttcccaact tatagtaatt taggaaagga tgatcatgat   2400
ttagaacatt cagcaaaaaa tttttataac atatctaatg agaatggcga taatacattc   2460
aataataata acaacaatat ggataacaag aaacgtatgt ataattataa taaacataaa   2520
gataatgata gcagatatac agataattct aacaaaaata gagataattc taacaaaaat   2580
agagataatt ataatagaaa caaagataaa aataacacaa atagggataa ttacaacaga   2640
tataaagata ataattacta ttataataat agtgataata ataactataa tgaaagaaaa   2700
cgctatatta ggaaaaaaac atacaataaa ttaagttatt ttaatttacc aagcttaaaa   2760
tcaatatata ataataaaat taagggaaat agtgaagaat tctcatttga taatgaatta   2820
cctgaacaaa ctgaatcgtt tcctttaaat aaaccacaag atcatgaagc attttataat   2880
ttaaaaaaac atcataccaa tgtgtatgaa ccaaatgatg aagaaaagca aaatgaacaa   2940
aaattgaagg atcaaattaa gattacatca gatattttat ataaagatat tgaagaaaat   3000
aaaaatacgg aagatgtctt attaatagaa actataacta ttaataatgg aactacatca   3060
aatacaattg aaaataataa ggatagtaat aaggaagcag aaaattctaa cactgaacaa   3120
aatgataata ataacaatga taataataac aacataaata ataataataa taataatgat   3180
aataaggaag aggatatgaa tgagaacaat aataattcaa aagttacagg tgacagtgta   3240
gaaaatatca atgaacaaac aaataataat caatatccaa acactgaata taataccata   3300
caaagatcta ttaatgcaaa atatttgatt ttcttttta aaaatcttca tgtatggaaa   3360
acagatttat tttgccagaa tataaattat atgaataact acctaaatag tatacaatat   3420
aataaaactc tcacctttga tataaattat gacacaaatg cagtaactat atattttact   3480
gataatatta cttatactgt aaaagtaaac ttagaatatc ttgtattttt attagaaaaa   3540
atatcattga taacatttgt agaagattta tgttctctct ttgatactga taaaaaaaga   3600
aattataaaa atttaactga attcttagaa aatacagaac gtataaatac atttgttaga   3660
aatcatatga tgttgtctaa tgaacaattt ataaataaaa ataaatatgc taaggaatta   3720
gcagaaatat ctacatctaa tctcttttat cctaaaaaag atattatttt aagatccaca   3780
ccttataaca atattatatt agatgaaaaa gatatatacc aaactatttt tatttatatg   3840
gatgatatgt taacagaaaa aatggtaaat gatacttgga ttacacctta cgcctttgta   3900
gtctattcaa aatccaaaaa agacatgcaa ggaaataata ttaaaatcga acaaaataag   3960
aatataacca aatattctag aagtgcaatt gataaatatg tgcattatga atataaaaga   4020
atttcagaaa acctaaatcg ctttttttatg gaatcaaatt caaatgctcc tcaatttaat   4080
gaaaattata aagaatatac aataattatt tataatgata atccatctat gcctaatatt   4140
gtacttacta caacgattaa tgtattcaat gtttctttct tacaaagcat aatggaaatg   4200
```

-continued ttattaaata ttaaagccaa ccaacaattc ttttcttata aaggaaaatt cataccaatc 4260
aatgcattca ttactttaga aaataaaatc aactacatat tctttaacta tataccactt 4320
gaaaattatg ttaataatgg agatgcacta gattttagaa atccatag 4368

<210> SEQ ID NO 4
<211> LENGTH: 1455
<212> TYPE: PRT
<213> ORGANISM: Plasmodium falciparum

<400> SEQUENCE: 4

Met Asn Arg Ile Phe Tyr Phe Cys Leu Phe Thr Ile Leu Phe Trp Leu
1 5 10 15

Ser Leu Val Ser Gly Glu Asn Val Asn Asn Lys Asn Cys Asn Glu Lys
20 25 30

Asn Arg Lys Ala Ile Leu Leu Ala Leu Leu Lys Asn Ser Leu Val Asp
35 40 45

Asn Lys Asp Tyr Asn Asn Ser Glu Glu Leu Lys Tyr Ala Leu Glu His
50 55 60

Ile Gln Asn Ser Glu Leu Tyr Pro Lys Asp Ser Lys Lys Phe Asp Lys
65 70 75 80

Phe Ile Asp Glu Phe Phe Ser Tyr Tyr Asn Ile His Val Asn Phe Thr
85 90 95

Asp Glu Glu Lys Arg Ile Leu His Ile Ser Gly Val Phe Lys Glu Phe
100 105 110

Tyr Val Asp Val Asp Asn Leu Asn Lys Asp Glu Met Lys Glu Tyr Phe
115 120 125

Lys Lys Asn Tyr Glu Lys Gly Leu Ser Leu Ile Asn Leu Ile Val His
130 135 140

Ser Asn Leu Ile Ile Gln Gln Phe Asp His Asp Ile Ile Asp Lys Lys
145 150 155 160

Lys Val His Glu Gln Asn Thr Asn Thr Asn Lys Thr Leu Glu Tyr Ile
165 170 175

Ser Asp Asn Leu Asn Asp Leu Ile Asn Phe Lys Asn Ile His Leu Asn
180 185 190

Asn Asn Ser Thr Gly Asp Phe Ile Ile Lys Leu Tyr Thr Asn Tyr Val
195 200 205

Asn Tyr Ile Asn Pro Tyr Gln Thr Asn Pro Leu Pro Asn Thr Pro His
210 215 220

Tyr Tyr Glu His Lys Asn Phe His Thr Lys Glu His Tyr Ile Tyr Asp
225 230 235 240

Glu Glu Ile Val Asn Pro Asn Met Asp Asn Ile Asn Thr His Thr Glu
245 250 255

Glu Asp Asn Val Tyr Val Ser Ala Thr Lys Gly Asn Gln Lys Glu Glu
260 265 270

Thr Glu Lys Lys Glu Asn His Glu Asn Asn Asn Ala Ile Asn Pro Lys
275 280 285

Tyr Met Asn Tyr Glu Thr Tyr Tyr Lys Lys Ile Phe Asn Ala Ile Phe
290 295 300

Glu Gln Ile Asp Lys Leu Asn Lys Thr Leu Phe Glu Ile Lys Asn Lys
305 310 315 320

Asn Asn Ser Glu Thr Asn Glu Asn Ile Ser Glu Ser Asn Ser Gly Asn
325 330 335

Pro Glu Leu Asn Asn Glu Asn Ser Tyr Ser Val Lys Leu Ser Ser Ser

-continued

```
            340                 345                 350

Ser Pro Asn Ser Thr Asn Lys Glu Ser Leu Ile Phe Pro Tyr Thr Tyr
        355                 360                 365

Tyr Asn Pro Tyr Tyr Met Phe Arg Leu Thr Asn Asn Phe Lys Glu Asn
    370                 375                 380

Asp Glu Gly Leu Lys Asn Glu Asn Asn Ile Asn Asn Asn Glu Asp Asn
385                 390                 395                 400

Gln Asn Asp Asn Met Asn Ile Val Leu Gly Lys Ile His Asn Ile Leu
                405                 410                 415

Lys Asp Phe Asn Ile Asn Glu Asn Ile Met Thr Asn Lys Met Ser Ala
            420                 425                 430

Pro Leu Ile Met Thr Ile Ile Leu Asn Phe Phe Lys Lys Tyr Met Ala
        435                 440                 445

Glu Asn Lys Phe Asn Leu Pro Met Ser Ser Glu Val Glu Asn Lys Ile
    450                 455                 460

Asn Lys Ser Asn Asn Lys Ala Leu Leu Gln Gln Ser Asn Lys Asp Thr
465                 470                 475                 480

Pro Ile His Lys Lys Lys Glu Ile Arg Asn Lys Lys Ile Gln Thr Lys
                485                 490                 495

Val Asp Val Ile Asp Glu Lys Thr Lys Lys Lys Ile Ala Asn Thr Ile
            500                 505                 510

Tyr Val Asn Val Gly Gln Ser Gly Ile Asn Gly Phe Phe Asn Phe Phe
        515                 520                 525

Asp Phe Arg Glu Lys Ser Ile Asp Ser Asn Ile Phe Asp Leu Leu His
    530                 535                 540

Val Met Glu Asp Met Lys Ile Phe Asp Ile Phe Gln Thr Ile Ile Phe
545                 550                 555                 560

Ile Gln Lys Phe Thr Glu Asn Val Cys Ala Ser Tyr Cys Met Asn Ile
                565                 570                 575

Thr Asp Val Leu Glu Leu Ser His Tyr Asp Met Ile Phe Tyr Asp Lys
            580                 585                 590

Met Val Phe His Phe Ser Lys Asp Gly Met Met Ile Lys Thr Asp Lys
        595                 600                 605

Lys Tyr Leu Tyr Asn Leu Lys Glu Phe Glu Asn Ile Leu Asn Leu Leu
    610                 615                 620

Asn Ile Asn Ala Asn Thr Ile Ala Leu Asn Cys Thr Cys Lys Phe Tyr
625                 630                 635                 640

Val Asp Val Asn Tyr Thr Tyr Ser Glu Gln Tyr Lys Met His Leu Lys
                645                 650                 655

Gly Tyr Leu His Lys Met Asn Glu Phe Asp Tyr Ile Asn Asn Phe Ser
            660                 665                 670

Ala Ser Tyr Leu Leu Asn Gln Leu Ile Ile Phe Gln Asp Lys Phe Asn
        675                 680                 685

Tyr Ile Lys Met Asn Gly Lys Leu Pro Ile Asp Asp Pro Lys Asn Ile
    690                 695                 700

Tyr Asn Met Asn Asn Val His Asp Thr Ala Tyr Tyr His Asn Ser Arg
705                 710                 715                 720

Tyr Phe Pro Thr Lys Asp Met Pro Ser Leu Glu Asp Asn Phe Tyr Glu
                725                 730                 735

His Leu Lys Tyr Pro Asp Ile Asn Thr Ile His Ile Tyr Tyr Asn Ala
            740                 745                 750

Ser Pro Val Lys Leu Asn Glu Val Asn Asp Leu Lys Thr Ile Ile Ile
        755                 760                 765
```

-continued

```
Asp Glu Ile Lys Ser Lys Ile Phe Tyr Ile Asn Ser Tyr Arg Val Gly
    770                 775                 780

Asp Gln Phe Phe Pro Thr Tyr Ser Asn Leu Gly Lys Asp Asp His Asp
785                 790                 795                 800

Leu Glu His Ser Ala Lys Asn Phe Tyr Asn Ile Ser Asn Glu Asn Gly
                805                 810                 815

Asp Asn Thr Phe Asn Asn Asn Asn Asn Asn Met Asp Asn Lys Lys Arg
            820                 825                 830

Met Tyr Asn Tyr Asn Lys His Lys Asp Asn Asp Ser Arg Tyr Thr Asp
        835                 840                 845

Asn Ser Asn Lys Asn Arg Asp Asn Ser Asn Lys Asn Arg Asp Asn Tyr
    850                 855                 860

Asn Arg Asn Lys Asp Lys Asn Asn Thr Asn Arg Asp Asn Tyr Asn Arg
865                 870                 875                 880

Tyr Lys Asp Asn Asn Tyr Tyr Tyr Asn Asn Ser Asp Asn Asn Asn Tyr
                885                 890                 895

Asn Glu Arg Lys Arg Tyr Ile Arg Lys Lys Thr Tyr Asn Lys Leu Ser
            900                 905                 910

Tyr Phe Asn Leu Pro Ser Leu Lys Ser Ile Tyr Asn Asn Lys Ile Lys
        915                 920                 925

Gly Asn Ser Glu Glu Phe Ser Phe Asp Asn Glu Leu Pro Glu Gln Thr
    930                 935                 940

Glu Ser Phe Pro Leu Asn Lys Pro Gln Asp His Glu Ala Phe Tyr Asn
945                 950                 955                 960

Leu Lys Lys His His Thr Asn Val Tyr Glu Pro Asn Asp Glu Glu Lys
                965                 970                 975

Gln Asn Glu Gln Lys Leu Lys Asp Gln Ile Lys Ile Thr Ser Asp Ile
            980                 985                 990

Leu Tyr Lys Asp Ile Glu Glu Asn  Lys Asn Thr Glu Asp  Val Leu Leu
        995                 1000                1005

Ile Glu  Thr Ile Thr Ile Asn  Asn Gly Thr Thr Ser  Asn Thr Ile
    1010                1015                1020

Glu Asn  Asn Lys Asp Ser Asn  Lys Glu Ala Glu Asn  Ser Asn Thr
    1025                1030                1035

Glu Gln  Asn Asp Asn Asn Asn  Asn Asp Asn Asn Asn  Asn Ile Asn
    1040                1045                1050

Asn Asn  Asn Asn Asn Asn Asp  Asn Lys Glu Glu Asp  Met Asn Glu
    1055                1060                1065

Asn Asn  Asn Asn Ser Lys Val  Thr Gly Asp Ser Val  Glu Asn Ile
    1070                1075                1080

Asn Glu  Gln Thr Asn Asn Asn  Gln Tyr Pro Asn Thr  Glu Tyr Asn
    1085                1090                1095

Thr Ile  Gln Arg Ser Ile Asn  Ala Lys Tyr Leu Ile  Phe Phe Phe
    1100                1105                1110

Lys Asn  Leu His Val Trp Lys  Thr Asp Leu Phe Cys  Gln Asn Ile
    1115                1120                1125

Asn Tyr  Met Asn Asn Tyr Leu  Asn Ser Ile Gln Tyr  Asn Lys Thr
    1130                1135                1140

Leu Thr  Phe Asp Ile Asn Tyr  Asp Thr Asn Ala Val  Thr Ile Tyr
    1145                1150                1155

Phe Thr  Asp Asn Ile Thr Tyr  Thr Val Lys Val Asn  Leu Glu Tyr
    1160                1165                1170
```

-continued

```
Leu Val  Phe Leu Leu Glu Lys  Ile Ser Leu Ile Thr  Phe Val Glu
    1175                 1180                 1185

Asp Leu  Cys Ser Leu Phe Asp  Thr Asp Lys Lys Arg  Asn Tyr Lys
    1190                 1195                 1200

Asn Leu  Thr Glu Phe Leu Glu  Asn Thr Glu Arg Ile  Asn Thr Phe
    1205                 1210                 1215

Val Arg  Asn His Met Met Leu  Ser Asn Glu Gln Phe  Ile Asn Lys
    1220                 1225                 1230

Asn Lys  Tyr Ala Lys Glu Leu  Ala Glu Ile Ser Thr  Ser Asn Leu
    1235                 1240                 1245

Phe Tyr  Pro Lys Lys Asp Ile  Ile Leu Arg Ser Thr  Pro Tyr Asn
    1250                 1255                 1260

Asn Ile  Ile Leu Asp Glu Lys  Asp Ile Tyr Gln Thr  Ile Phe Ile
    1265                 1270                 1275

Tyr Met  Asp Asp Met Leu Thr  Glu Lys Met Val Asn  Asp Thr Trp
    1280                 1285                 1290

Ile Thr  Pro Tyr Ala Phe Val  Val Tyr Ser Lys Ser  Lys Lys Asp
    1295                 1300                 1305

Met Gln  Gly Asn Asn Ile Lys  Ile Glu Gln Asn Lys  Asn Ile Thr
    1310                 1315                 1320

Lys Tyr  Ser Arg Ser Ala Ile  Asp Lys Tyr Val His  Tyr Glu Tyr
    1325                 1330                 1335

Lys Arg  Ile Ser Glu Asn Leu  Asn Arg Phe Phe Met  Glu Ser Asn
    1340                 1345                 1350

Ser Asn  Ala Pro Gln Phe Asn  Glu Asn Tyr Lys Glu  Tyr Thr Ile
    1355                 1360                 1365

Ile Ile  Tyr Asn Asp Asn Pro  Ser Met Pro Asn Ile  Val Leu Thr
    1370                 1375                 1380

Thr Thr  Ile Asn Val Phe Asn  Val Ser Phe Leu Gln  Ser Ile Met
    1385                 1390                 1395

Glu Met  Leu Leu Asn Ile Lys  Ala Asn Gln Gln Phe  Phe Ser Tyr
    1400                 1405                 1410

Lys Gly  Lys Phe Ile Pro Ile  Asn Ala Phe Ile Thr  Leu Glu Asn
    1415                 1420                 1425

Lys Ile  Asn Tyr Ile Phe Phe  Asn Tyr Ile Pro Leu  Glu Asn Tyr
    1430                 1435                 1440

Val Asn  Asn Gly Asp Ala Leu  Asp Phe Arg Asn Pro
    1445                 1450                 1455
```

<210> SEQ ID NO 5
<211> LENGTH: 1652
<212> TYPE: DNA
<213> ORGANISM: Plasmodium falciparum

<400> SEQUENCE: 5

```
atgaaccttt tagttttttt ttgtttttttc cttttatcgt gcatagtcca tctttcaaga      60

tgttcaggta aaaataataa aaactgctaa gagaaaaaaa aaaaaaaaaa aaaaaaaaaa     120

aaaaaaacaa tatatatata tatatatata tataacaata tatgttatat tattttttat     180

tgcgtttttg tggaaatagt gttcattctt gtgttggcat aggaaaatga taaatcaaaa     240

tatattgata tatatataga aaattattat gtatattata ttatatttta tttttttttt     300

ttccttgaat ataaaaaaaa aaaagaaatt attaaagtgt gaaatattat atagaatata     360

ttaataaatt aatatattat tattttattt tatatgaatt gaattatata tatatatata     420
```

-continued

```
tatatatata tatatattta tttatttatt tttgtaccga tttgtatccc tttatagata    480

ataacagcta ctcatttgaa attgtgaata gatctacgtg gttaaatata gcagagagaa    540

tattcaaagg aaacgctcca tttaatttta caataattcc atataattat gtaaataatt    600

ctacagaaga aaataataat aaagattcag ttttattaat aagtaagaat ttaaaaaatt    660

cttccaatcc tgttgatgaa aataatcata taattgacag tacaaaaaaa aacacatcga    720

ataataataa taataatagt aatattgttg ggatatacga atctcaagta catgaagaaa    780

agataaaaga agataataca cgtcaggata atataaataa aaaggaaaac gaaataataa    840

ataataatca tcaaatacca gtatcaaata tttttcaga aaatattgat aataataaaa    900

attacattga atcaaattat aagagcacgt ataataataa tccagagttg attcattcaa    960

cagattttat tggttcaaat aataatcata catttaattt tctttcgaga tataataata   1020

gtgtattgaa caatatgcaa ggaaatacaa aagttccagg taacgttcct gaattaaaag   1080

ctagaatttt ttcagaagaa gaaaatactg aagtagaatc tgcagaaaat aatcatacga   1140

attcattaaa ccccaatgaa tcatgtgatc aaataataaa attaggtgat ataataaata   1200

gtgtaaatga aaaaatcata tctataaatt cgacagtaaa taatgtatta tgtataaatt   1260

tagattcagt aaatggaaat ggttttgtat ggactttatt aggagtacat aagaaaaaac   1320

cattgattga tccatctaat ttccctacaa aaagagtaac acaatcatat gttagtcctg   1380

atatttcagt gaccaatcca gtacctatac ctaaaaatag taatacgaac aaagatgatt   1440

caataaataa taaacaagat ggaagtcaaa ataacaccac aacaaatcat tttcctaagc   1500

ccagagaaca gctagtcgga ggctcatcca tgttaataag taaaattaag ccccacaaac   1560

ctggaaaata ttttattgtc tattcatatt atagaccatt tgatccaaca agggatacaa   1620

acacaagaat tgtagagtta aacgtgcaat aa                                 1652
```

<210> SEQ ID NO 6
<211> LENGTH: 413
<212> TYPE: PRT
<213> ORGANISM: Plasmodium falciparum

<400> SEQUENCE: 6

```
Met Asn Leu Leu Val Phe Phe Cys Phe Phe Leu Leu Ser Cys Ile Val
1               5                   10                  15

His Leu Ser Arg Cys Ser Asp Asn Asn Ser Tyr Ser Phe Glu Ile Val
            20                  25                  30

Asn Arg Ser Thr Trp Leu Asn Ile Ala Glu Arg Ile Phe Lys Gly Asn
        35                  40                  45

Ala Pro Phe Asn Phe Thr Ile Ile Pro Tyr Asn Tyr Val Asn Asn Ser
    50                  55                  60

Thr Glu Glu Asn Asn Asn Lys Asp Ser Val Leu Leu Ile Ser Lys Asn
65                  70                  75                  80

Leu Lys Asn Ser Ser Asn Pro Val Asp Glu Asn Asn His Ile Ile Asp
                85                  90                  95

Ser Thr Lys Lys Asn Thr Ser Asn Asn Asn Asn Asn Asn Ser Asn Ile
            100                 105                 110

Val Gly Ile Tyr Glu Ser Gln Val His Glu Glu Lys Ile Lys Glu Asp
        115                 120                 125

Asn Thr Arg Gln Asp Asn Ile Asn Lys Lys Glu Asn Glu Ile Ile Asn
    130                 135                 140

Asn Asn His Gln Ile Pro Val Ser Asn Ile Phe Ser Glu Asn Ile Asp
145                 150                 155                 160
```

```
Asn Asn Lys Asn Tyr Ile Glu Ser Asn Tyr Lys Ser Thr Tyr Asn Asn
                165                 170                 175

Asn Pro Glu Leu Ile His Ser Thr Asp Phe Ile Gly Ser Asn Asn Asn
            180                 185                 190

His Thr Phe Asn Phe Leu Ser Arg Tyr Asn Asn Ser Val Leu Asn Asn
        195                 200                 205

Met Gln Gly Asn Thr Lys Val Pro Gly Asn Val Pro Glu Leu Lys Ala
    210                 215                 220

Arg Ile Phe Ser Glu Glu Glu Asn Thr Glu Val Glu Ser Ala Glu Asn
225                 230                 235                 240

Asn His Thr Asn Ser Leu Asn Pro Asn Glu Ser Cys Asp Gln Ile Ile
                245                 250                 255

Lys Leu Gly Asp Ile Ile Asn Ser Val Asn Glu Lys Ile Ile Ser Ile
            260                 265                 270

Asn Ser Thr Val Asn Asn Val Leu Cys Ile Asn Leu Asp Ser Val Asn
        275                 280                 285

Gly Asn Gly Phe Val Trp Thr Leu Leu Gly Val His Lys Lys Lys Pro
    290                 295                 300

Leu Ile Asp Pro Ser Asn Phe Pro Thr Lys Arg Val Thr Gln Ser Tyr
305                 310                 315                 320

Val Ser Pro Asp Ile Ser Val Thr Asn Pro Val Pro Ile Pro Lys Asn
                325                 330                 335

Ser Asn Thr Asn Lys Asp Asp Ser Ile Asn Asn Lys Gln Asp Gly Ser
            340                 345                 350

Gln Asn Asn Thr Thr Thr Asn His Phe Pro Lys Pro Arg Glu Gln Leu
        355                 360                 365

Val Gly Gly Ser Ser Met Leu Ile Ser Lys Ile Lys Pro His Lys Pro
    370                 375                 380

Gly Lys Tyr Phe Ile Val Tyr Ser Tyr Tyr Arg Pro Phe Asp Pro Thr
385                 390                 395                 400

Arg Asp Thr Asn Thr Arg Ile Val Glu Leu Asn Val Gln
                405                 410
```

```
<210> SEQ ID NO 7
<211> LENGTH: 1662
<212> TYPE: DNA
<213> ORGANISM: Plasmodium falciparum

<400> SEQUENCE: 7

atgaaaagta gaaacaatat tcatcatcat aaaaagaaaa acgaagttaa taatacactg      60

gaagaatata aggacataat accagatatt gaaattcaaa ttgagaactt attaaaaaaa     120

tttcatatta caaaatatga ttataaaatt actcattttt taattgacat aatacaaaat     180

gaatctctta aaatattaaa aaatgctaag catataaaga agaatatata ttataataat     240

tataatgata aggatgataa tataaattat tataatatta atgatgaaca tataaataat     300

aatgaaaata atgataatat ttataatgtg aaagaaaatg cgcatataaa ccatgataca     360

ttatacgaag aaaaatatat acaaaaagag gaaggaacaa ttaaccatat aaataataat     420

acagatatgg aaaatataaa tgaaaacaac tcaccgaata aatgtagttc acacatgtta     480

aatgatttat tgaacaattt taatgaagat agtgctatag aaaaaaactc acacattgat     540

gtagttaata atatggagga cgaaaaggtt aacataaatg atgctgaaaa gattgataat     600

gaaaagatta atgatgaaaa aaatgatgct gaacaaatta atgatgaaaa aaatgatgat     660
```

-continued

```
gaaaaaaatg atgatgaaaa aaatgatgat gaaaaaaatg atgctgaaca aattaatgat    720

gaaaaaaatg atgatgaaaa aaatgatgat gaaaaaaatg atgatgaaaa aaatgatgat    780

gaaaaaatta atgatgaaaa aaatgatgat gaaaaaaatg atgatgaaaa aaatgatgat    840

gaaaaaaatg atgatgaaaa aattgatgct gaacaaatta atgatgaaca aattaatgct    900

gaacaaatta acgatgaaca aattaatgat gaacaaatta acgatgaaaa aattaacgat    960

gaacaaatta acgatgaaaa aattaacgat gaacaaatta atgatgaaaa aattaacgat   1020

gaacaaatta atgatgaaaa aattaacgat gaacaaatta atgatgaaaa aattaacgat   1080

gaacaaatta atgatgaaaa aattaacgat gaacaaatta atgatgaaca aattaatgat   1140

gaacaaatta atgatgataa tatttcaaat aaaccggaat tatcattatc ggatattttt   1200

aatactatcg aatgcacaag taataatatc caagagcaag aaaataaaga cgaattaatt   1260

aataaggata taccatccaa taataaaact gataataaag aaaataatca tattcctaaa   1320

aataatcctc taaactgtaa tgacaataat caaaaaaatt tacaaaatat tggtaataat   1380

aaaaataaaa tacgtgatga agtattaata attgatgaag aaagtgtaaa tctagccatt   1440

aaagaatatg tcctcaaaac aatatataga aagaaaaatg tagatttctt atatgaaaaa   1500

ttggaatttc aacaaaagga caaccttatg gttaatagaa atataaaata tccatccggt   1560

cttcctccat atttaccaga tgattgttct gttaatacca tattaccatc atgggatata   1620

aaatataact tcaattcttc aaaaagaaag attaaaaaat aa                      1662
```

<210> SEQ ID NO 8
<211> LENGTH: 553
<212> TYPE: PRT
<213> ORGANISM: Plasmodium falciparum

<400> SEQUENCE: 8

```
Met Lys Ser Arg Asn Asn Ile His His His Lys Lys Lys Asn Glu Val
1               5                   10                  15

Asn Asn Thr Leu Glu Glu Tyr Lys Asp Ile Ile Pro Asp Ile Glu Ile
            20                  25                  30

Gln Ile Glu Asn Leu Leu Lys Lys Phe His Ile Thr Lys Tyr Asp Tyr
        35                  40                  45

Lys Ile Thr His Phe Leu Ile Asp Ile Ile Gln Asn Glu Ser Leu Lys
    50                  55                  60

Ile Leu Lys Asn Ala Lys His Ile Lys Lys Asn Ile Tyr Tyr Asn Asn
65                  70                  75                  80

Tyr Asn Asp Lys Asp Asp Asn Ile Asn Tyr Tyr Asn Ile Asn Asp Glu
                85                  90                  95

His Ile Asn Asn Asn Glu Asn Asn Asp Asn Ile Tyr Asn Val Lys Glu
            100                 105                 110

Asn Ala His Ile Asn His Asp Thr Leu Tyr Glu Glu Lys Tyr Ile Gln
        115                 120                 125

Lys Glu Glu Gly Thr Ile Asn His Ile Asn Asn Asn Thr Asp Met Glu
    130                 135                 140

Asn Ile Asn Glu Asn Asn Ser Pro Asn Lys Cys Ser Ser His Met Leu
145                 150                 155                 160

Asn Asp Leu Leu Asn Asn Phe Asn Glu Asp Ser Ala Ile Glu Lys Asn
                165                 170                 175

Ser His Ile Asp Val Val Asn Asn Met Glu Asp Glu Lys Val Asn Ile
            180                 185                 190

Asn Asp Ala Glu Lys Ile Asp Asn Glu Lys Ile Asn Asp Glu Lys Asn
```

-continued

```
        195                 200                 205

Asp Ala Glu Gln Ile Asn Asp Glu Lys Asn Asp Asp Glu Lys Asn Asp
    210                 215                 220

Asp Glu Lys Asn Asp Asp Glu Lys Asn Asp Ala Glu Gln Ile Asn Asp
225                 230                 235                 240

Glu Lys Asn Asp Asp Glu Lys Asn Asp Asp Glu Lys Asn Asp Asp Glu
                245                 250                 255

Lys Asn Asp Asp Glu Lys Ile Asn Asp Glu Lys Asn Asp Asp Glu Lys
            260                 265                 270

Asn Asp Asp Glu Lys Asn Asp Asp Glu Lys Asn Asp Asp Glu Lys Ile
        275                 280                 285

Asp Ala Glu Gln Ile Asn Asp Glu Gln Ile Asn Ala Glu Gln Ile Asn
    290                 295                 300

Asp Glu Gln Ile Asn Asp Glu Gln Ile Asn Asp Glu Lys Ile Asn Asp
305                 310                 315                 320

Glu Gln Ile Asn Asp Glu Lys Ile Asn Asp Glu Gln Ile Asn Asp Glu
                325                 330                 335

Lys Ile Asn Asp Glu Gln Ile Asn Asp Glu Lys Ile Asn Asp Glu Gln
            340                 345                 350

Ile Asn Asp Glu Lys Ile Asn Asp Glu Gln Ile Asn Asp Glu Lys Ile
        355                 360                 365

Asn Asp Glu Gln Ile Asn Asp Glu Gln Ile Asn Asp Glu Gln Ile Asn
    370                 375                 380

Asp Asp Asn Ile Ser Asn Lys Pro Glu Leu Ser Leu Ser Asp Ile Phe
385                 390                 395                 400

Asn Thr Ile Glu Cys Thr Ser Asn Asn Ile Gln Glu Gln Glu Asn Lys
                405                 410                 415

Asp Glu Leu Ile Asn Lys Asp Ile Pro Ser Asn Asn Lys Thr Asp Asn
            420                 425                 430

Lys Glu Asn Asn His Ile Pro Lys Asn Asn Pro Leu Asn Cys Asn Asp
        435                 440                 445

Asn Asn Gln Lys Asn Leu Gln Asn Ile Gly Asn Asn Lys Asn Lys Ile
    450                 455                 460

Arg Asp Glu Val Leu Ile Ile Asp Glu Glu Ser Val Asn Leu Ala Ile
465                 470                 475                 480

Lys Glu Tyr Val Leu Lys Thr Ile Tyr Arg Lys Lys Asn Val Asp Phe
                485                 490                 495

Leu Tyr Glu Lys Leu Glu Phe Gln Gln Lys Asp Asn Leu Met Val Asn
            500                 505                 510

Arg Asn Ile Lys Tyr Pro Ser Gly Leu Pro Pro Tyr Leu Pro Asp Asp
        515                 520                 525

Cys Ser Val Asn Thr Ile Leu Pro Ser Trp Asp Ile Lys Tyr Asn Phe
    530                 535                 540

Asn Ser Ser Lys Arg Lys Ile Lys Lys
545                 550
```

<210> SEQ ID NO 9
<211> LENGTH: 702
<212> TYPE: DNA
<213> ORGANISM: Plasmodium falciparum

<400> SEQUENCE: 9

```
atgtttcggt cgaaggctca ttttttgatg ctagccaatt taaagtattt ggagttacaa      60

gacttattgt tgaaaagatt tcaagtattt aaaaatgagg aaataagaat attaaaaaaa     120
```

```
gagaacatga aacgtatttt atatgaatgg gccaagtttc taataaaaga aaatgataat    180

acaaatataa catacatacc acaaaaagta ttacaaaata ataaagttca agatatatta    240

aaaaatgata tagattgtga atggctagta aataaaattc atatatcaaa tgatgaacaa    300

ataaatattc attcttctaa taattttgag gaattcaaaa aaaaaaaaga tgctctccat    360

tttgatgaat atccaaattt attttattat gaatatccac aatttcctta taattattat    420

gataaaaaaa aaatgtctaa tttttattct cttatcaaat ttccatatca agatatttta    480

aacatttcaa aaaatataaa aaatatgtca aaggaggaag aacaaaaaaa ggaaaatcat    540

caaatcaaca ataatgtatc taataacgaa gaaaataaaa taaatcaaga tattgtacat    600

atgaataata ataatgttaa ttatacagat catagttatg tgtatgctcc atgcgaaatg    660

gaaacatcaa aggaaaatta taaccaaaca caaatagatt aa                        702


<210> SEQ ID NO 10
<211> LENGTH: 233
<212> TYPE: PRT
<213> ORGANISM: Plasmodium falciparum

<400> SEQUENCE: 10

Met Phe Arg Ser Lys Ala His Phe Leu Met Leu Ala Asn Leu Lys Tyr
1               5                   10                  15

Leu Glu Leu Gln Asp Leu Leu Leu Lys Arg Phe Gln Val Phe Lys Asn
            20                  25                  30

Glu Glu Ile Arg Ile Leu Lys Lys Glu Asn Met Lys Arg Ile Leu Tyr
        35                  40                  45

Glu Trp Ala Lys Phe Leu Ile Lys Glu Asn Asp Asn Thr Asn Ile Thr
    50                  55                  60

Tyr Ile Pro Gln Lys Val Leu Gln Asn Asn Lys Val Gln Asp Ile Leu
65                  70                  75                  80

Lys Asn Asp Ile Asp Cys Glu Trp Leu Val Asn Lys Ile His Ile Ser
                85                  90                  95

Asn Asp Glu Gln Ile Asn Ile His Ser Ser Asn Asn Phe Glu Glu Phe
            100                 105                 110

Lys Lys Lys Lys Asp Ala Leu His Phe Asp Glu Tyr Pro Asn Leu Phe
        115                 120                 125

Tyr Tyr Glu Tyr Pro Gln Phe Pro Tyr Asn Tyr Tyr Asp Lys Lys Lys
    130                 135                 140

Met Ser Asn Phe Tyr Ser Leu Ile Lys Phe Pro Tyr Gln Asp Ile Leu
145                 150                 155                 160

Asn Ile Ser Lys Asn Ile Lys Asn Met Ser Lys Glu Glu Glu Gln Lys
                165                 170                 175

Lys Glu Asn His Gln Ile Asn Asn Asn Val Ser Asn Asn Glu Glu Asn
            180                 185                 190

Lys Ile Asn Gln Asp Ile Val His Met Asn Asn Asn Asn Val Asn Tyr
        195                 200                 205

Thr Asp His Ser Tyr Val Tyr Ala Pro Cys Glu Met Glu Thr Ser Lys
    210                 215                 220

Glu Asn Tyr Asn Gln Thr Gln Ile Asp
225                 230


<210> SEQ ID NO 11
<211> LENGTH: 1183
<212> TYPE: DNA
<213> ORGANISM: Plasmodium falciparum
```

<400> SEQUENCE: 11

```
catgatttt acacattgat aaattaagaa acattatata aattttgttc ttcaaaaata     60
taaaagtttt aattttcaac taaacatttc tttttgtata tgtgtgtgta tgtactactt    120
aaatagaaca aaatgaataa atttacatat tgtattaccc tcttgatagc attagttctt    180
cctataagat ctatacaact tcattctgta aattatgctc ccttgaatta tattgaaagt    240
aatattaact gcattgtttt atacatatta atatatatat atatatattt acaatatgta    300
aaaatatatt gaatatgaat ggaacacaca tatatatata tatatatatt tatatatata    360
tttatatttt tttttcagtt ggagacacac tttccaataa agttggtgaa ttatggcata    420
gccatttaaa ctcattcata gacattgtat ctacaaaagt tgttaacaaa ttggaagatg    480
atttatcaaa tggaaataat ttggaaaaat tcatgattct tttagaggta atacgaatga    540
tacttatgtt atacatatat taatatttta catagacaat agatacatat atttacttta    600
attgaattgt attaattact ggtttttaat tattttgttt atatatatat atatatatat    660
atatatatat ttttttttt tttttttata ggatgatgca gacatctttg atgcaagcgc    720
atacgagggg aaaaatcttg cacttataca aacagaattt ataagaaaat taaaggacaa    780
atttaaaaat agtaaatttg gacaaaaatt aaagaaactt ggatcaaagg caaaggaaaa    840
gcttcttagt ttgtatcaaa aacataaagg aaaactcaga catttcttta gcatacttct    900
taaaagctta gtcattccaa tagctgttca atttatacga aaaaatttaa acaaatggaa    960
acaaagaaca ttagaagcta ctcagaaact tgatgaacaa tcaaagaata tagcacaacc   1020
aattataaat agattatata acagtttcga agacaaaatt gaagaatatt ctcaagaaaa   1080
taaaataaat gtagaagatg aattaaatgc tcttggacaa ttagataagg ataagcaaga   1140
tatacaaaaa ttagaagagc aagaaaaagc cctattacaa taa                     1183
```

<210> SEQ ID NO 12
<211> LENGTH: 248
<212> TYPE: PRT
<213> ORGANISM: Plasmodium falciparum

<400> SEQUENCE: 12

```
Met Asn Lys Phe Thr Tyr Cys Ile Thr Leu Leu Ile Ala Leu Val Leu
1               5                   10                  15

Pro Ile Arg Ser Ile Gln Leu His Ser Val Asn Tyr Ala Pro Leu Asn
            20                  25                  30

Tyr Ile Glu Ile Gly Asp Thr Leu Ser Asn Lys Val Gly Glu Leu Trp
        35                  40                  45

His Ser His Leu Asn Ser Phe Ile Asp Ile Val Ser Thr Lys Val Val
    50                  55                  60

Asn Lys Leu Glu Asp Asp Leu Ser Asn Gly Asn Asn Leu Glu Lys Phe
65                  70                  75                  80

Met Ile Leu Leu Glu Asp Asp Ala Asp Ile Phe Asp Ala Ser Ala Tyr
                85                  90                  95

Glu Gly Lys Asn Leu Ala Leu Ile Gln Thr Glu Phe Ile Arg Lys Leu
            100                 105                 110

Lys Asp Lys Phe Lys Asn Ser Lys Phe Gly Gln Lys Leu Lys Lys Leu
        115                 120                 125

Gly Ser Lys Ala Lys Glu Lys Leu Leu Ser Leu Tyr Gln Lys His Lys
    130                 135                 140

Gly Lys Leu Arg His Phe Phe Ser Ile Leu Leu Lys Ser Leu Val Ile
```

-continued

```
145                 150                 155                 160

Pro Ile Ala Val Gln Phe Ile Arg Lys Asn Leu Asn Lys Trp Lys Gln
                165                 170                 175

Arg Thr Leu Glu Ala Thr Gln Lys Leu Asp Glu Gln Ser Lys Asn Ile
            180                 185                 190

Ala Gln Pro Ile Ile Asn Arg Leu Tyr Asn Ser Phe Glu Asp Lys Ile
        195                 200                 205

Glu Glu Tyr Ser Gln Glu Asn Lys Ile Asn Val Glu Asp Glu Leu Asn
    210                 215                 220

Ala Leu Gly Gln Leu Asp Lys Asp Lys Gln Asp Ile Gln Lys Leu Glu
225                 230                 235                 240

Glu Gln Glu Lys Ala Leu Leu Gln
                245


<210> SEQ ID NO 13
<211> LENGTH: 690
<212> TYPE: DNA
<213> ORGANISM: Plasmodium falciparum

<400> SEQUENCE: 13

atgaaggtct ctaaattagt cttgtttgcg cacatatttt ttattataaa tatcttatgt      60

caatatattt gtttaaatgc ttctaaagta aataaaaagg gtaaaatagc agaagaaaag     120

aaaagaaaaa atattaaaaa cattgataaa gcaatagaag aacacaacaa aaggaagaaa     180

ctaatttatt attcattgat agcatctggg gcaatagcat cggttgcggc aatattggga     240

ttaggatatt atggatataa aaaatcgcga gaagatgatt tatattataa taaatatttg     300

gaatatagaa atggagaata caatataaaa tatcaagatg gtgctatagc aagtactagt     360

gaattttata tagaacctga aggaataaat aaaataaatt taaataaacc cataattgaa     420

aataaaaata atgtagatgt gtcaattaaa agatataata attttgtaga tatagcacga     480

cttagtatac aaaaacattt tgaacattta tcaaatgatc aaaaagattc tcatgtaaat     540

aacatggaat atatgcaaaa atttgttcaa ggattacaag aaaatagaaa tatatctcta     600

tccaaatatc aagaaaataa agctgttatg gatttaaaat atcatttaca aaaagtttat     660

gctaattatt tatctcaaga agagaactaa                                      690


<210> SEQ ID NO 14
<211> LENGTH: 229
<212> TYPE: PRT
<213> ORGANISM: Plasmodium falciparum

<400> SEQUENCE: 14

Met Lys Val Ser Lys Leu Val Leu Phe Ala His Ile Phe Phe Ile Ile
1               5                   10                  15

Asn Ile Leu Cys Gln Tyr Ile Cys Leu Asn Ala Ser Lys Val Asn Lys
            20                  25                  30

Lys Gly Lys Ile Ala Glu Glu Lys Lys Arg Lys Asn Ile Lys Asn Ile
        35                  40                  45

Asp Lys Ala Ile Glu Glu His Asn Lys Arg Lys Lys Leu Ile Tyr Tyr
    50                  55                  60

Ser Leu Ile Ala Ser Gly Ala Ile Ala Ser Val Ala Ala Ile Leu Gly
65                  70                  75                  80

Leu Gly Tyr Tyr Gly Tyr Lys Lys Ser Arg Glu Asp Asp Leu Tyr Tyr
                85                  90                  95

Asn Lys Tyr Leu Glu Tyr Arg Asn Gly Glu Tyr Asn Ile Lys Tyr Gln
```

-continued

| | | | | | | | | | | | | | | | |
|---|---|---|---|---|---|---|---|---|---|---|---|---|---|---|---|
| | | | 100 | | | | | 105 | | | | | 110 | | |
| Asp | Gly | Ala | Ile | Ala | Ser | Thr | Ser | Glu | Phe | Tyr | Ile | Glu | Pro | Glu | Gly |
| | | 115 | | | | | 120 | | | | | 125 | | | |
| Ile | Asn | Lys | Ile | Asn | Leu | Asn | Lys | Pro | Ile | Ile | Glu | Asn | Lys | Asn | Asn |
| | 130 | | | | | 135 | | | | | 140 | | | | |
| Val | Asp | Val | Ser | Ile | Lys | Arg | Tyr | Asn | Asn | Phe | Val | Asp | Ile | Ala | Arg |
| 145 | | | | | 150 | | | | | 155 | | | | | 160 |
| Leu | Ser | Ile | Gln | Lys | His | Phe | Glu | His | Leu | Ser | Asn | Asp | Gln | Lys | Asp |
| | | | | 165 | | | | | 170 | | | | | 175 | |
| Ser | His | Val | Asn | Asn | Met | Glu | Tyr | Met | Gln | Lys | Phe | Val | Gln | Gly | Leu |
| | | | 180 | | | | | 185 | | | | | 190 | | |
| Gln | Glu | Asn | Arg | Asn | Ile | Ser | Leu | Ser | Lys | Tyr | Gln | Glu | Asn | Lys | Ala |
| | | 195 | | | | | 200 | | | | | 205 | | | |
| Val | Met | Asp | Leu | Lys | Tyr | His | Leu | Gln | Lys | Val | Tyr | Ala | Asn | Tyr | Leu |
| | 210 | | | | | 215 | | | | | 220 | | | | |
| Ser | Gln | Glu | Glu | Asn | | | | | | | | | | | |
| 225 | | | | | | | | | | | | | | | |